(12) United States Patent
Li et al.

(10) Patent No.: US 9,879,073 B2
(45) Date of Patent: *Jan. 30, 2018

(54) LUNG-TARGETING NANOBODIES AGAINST HUMAN PULMONARY SURFACTANT PROTEIN A AND A METHOD FOR PRODUCING THE SAME

(71) Applicant: Shanghai Pulmonary Hospital, Shanghai (CN)

(72) Inventors: Huiping Li, Shanghai (CN); Xian He, Shanghai (CN); Shanmei Wang, Shanghai (CN)

(73) Assignee: SHANGHAI PULMONARY HOSPITAL, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/652,767

(22) PCT Filed: Apr. 8, 2015

(86) PCT No.: PCT/CN2015/076119
§ 371 (c)(1),
(2) Date: Jul. 29, 2016

(87) PCT Pub. No.: WO2016/131212
PCT Pub. Date: Aug. 25, 2016

(65) Prior Publication Data
US 2017/0058021 A1    Mar. 2, 2017

(30) Foreign Application Priority Data
Feb. 16, 2015   (CN) .......................... 2015 1 0086499

(51) Int. Cl.
*C07K 16/18*    (2006.01)
(52) U.S. Cl.
CPC ........ *C07K 16/18* (2013.01); *C07K 2317/569* (2013.01)

(58) Field of Classification Search
CPC .............. C07K 16/18; C07K 2317/569; C07K 2317/22; A61K 2039/505
See application file for complete search history.

(56) References Cited

U.S. PATENT DOCUMENTS 9,228,010 B2 *    1/2016    Li ........................... C07K 16/18

OTHER PUBLICATIONS

Colman et al., Research in Immunology (145(1):33-35, 1994.*
Wu et al., J Mol Biol 294: 151-162, 1999.*

* cited by examiner

*Primary Examiner* — Phuong Huynh
(74) *Attorney, Agent, or Firm* — Fish IP Law, LLC; Robert D. Fish

(57) ABSTRACT

The present invention relates to the field of biochemistry and pharmaceutical technologies. The present invention provides nanobodies that bind to human pulmonary surfactant protein A (SP-A) as well as the preparing methods and use of the same. The nanobody comprise an amino acid sequence having the formula of $Q(x)_2LVESGG(x)_2V(x)_2G(x)SL(x)LS(x)_{24}E(x)_{n2}$ $KG(x)_4S(x)_{n3}T(x)_2Y(x)C(x)_{n4}S(x)_{n5}V(x)_{n6}R$; wherein x is amino acid; n2~n6 are positive integers; $1 \le n2 \le 21$; $1 \le n3 \le 19$; $1 \le n4 \le 50$; $1 \le n5 \le 22$; $1 \le n6 \le 8$. The present invention take fresh frozen sections of lung as antigen, gene sequences with high affinity with hSP-A were obtained by constructing an SP-A antibody library and affinity selection, and nanobodies with high affinity and small molecular weight were obtained by induced expression of the gene sequences through a prokaryotic expression vector. Immunohistochemistry and in vivo imaging in nude mice showed the nanobodies have high specificity for targeting lung tissue.

3 Claims, 7 Drawing Sheets

| First Position | Second Position | | | | Third Position |
|---|---|---|---|---|---|
| | U | C | A | G | |
| U | phenylalanine<br>phenylalanine<br>leucine<br>leucine | serine<br>serine<br>serine<br>serine | tyrosine<br>tyrosine<br>stop<br>stop | cysteine<br>cysteine<br>stop<br>tryptophan | U<br>C<br>A<br>G |
| C | leucine<br>leucine<br>leucine<br>leucine | proline<br>proline<br>proline<br>proline | histidine<br>histidine<br>glutamine<br>glutamine | arginine<br>arginine<br>arginine<br>arginine | U<br>C<br>A<br>G |
| A | isoleucine<br>isoleucine<br>isoleucine<br>methionine<br>(Start) | threonine<br>threonine<br>threonine<br>threonine | asparagine<br>asparagine<br>lysine<br>lysine | serine<br>serine<br>arginine<br>arginine | U<br>C<br>A<br>G |
| G | valine<br>valine<br>valine<br>valine<br>(Start) | alanine<br>alanine<br>alanine<br>alanine | aspartic acid<br>aspartic acid<br>glutamic acid<br>glutamic acid | glicine<br>glicine<br>glicine<br>glicine | U<br>C<br>A<br>G |

Figure 10

LUNG-TARGETING NANOBODIES AGAINST HUMAN PULMONARY SURFACTANT PROTEIN A AND A METHOD FOR PRODUCING THE SAME

FIELD OF THE INVENTION

The present invention relates to the field of biochemistry and pharmaceutical technologies, particularly to nanobodies that bind to human pulmonary surfactant protein A (SP-A) with specificity.

BACKGROUND OF THE INVENTION

In the beginning of 20th century, the Nobel Prize winner German scientist Paul Ehrlich proposed the idea of "magic bullet" for future drug development, i.e., an ideal drug that would selectively destroy diseased cells without affecting healthy cells. In the past several decades, scientists have been exploring to develop such ideal drugs.

In the 1970s, targeted drug delivery system were developed and widely used for the treatment of cancer. Meanwhile, with the advancement of research, new targeted drug delivery carriers have, emerged, the routes of administration have, been broadened, and targeted drug delivery system have been expanded to treat many diseases other than cancer.

Developing targeted drugs for respiratory diseases is one of the hotspots, and it is primarily focused on the following areas:

1. Targeted treatment of airway diseases by inhalation.

Starting in the early 1950s, inhaled corticosteroids have been used for the treatment of asthma and COPD. Since then, with the improvement in inhaled drugs and devices, inhaled corticosteroids have become the main therapeutic agents for the treatment of asthma and COPD. However, inhaled drugs are mainly suitable for topical treatment of airway diseases, and are not effective against parenchyma and interstitial lung diseases due to low bioavailability.

Passive lung-targeting drugs through drug carriers.
2. Currently, a variety of drug carriers such as liposomes, microparticles, microspheres are used in the research of lung-targeted drug delivery. However, these passive targeting drug carriers have poor tissue selectivity, and cannot avoid significant residue in the liver, spleen and other organs. Therefore, they don't achieve optimal targeting effect.

The ligand-receptor or antigen-antibody binding is a special recognition mechanism of the human body, and it has been reported that the mechanism could achieve active drug targeting to enhance drug efficacy and reduce the side effects. For example, a composite drug made of paclitaxel liposomes and a monoclonal antibodies against the epidermal growth factor has anti-tumor effect 25 times greater then that of the drug without the monoclonal antibody. Thus, to achieve ideal active lung targeting effect, it is critical to find a receptor in the lung tissue with high specificity and prepare a targeting ligand with high affinity. Studies have shown that pulmonary alveolar type II epithelial cells which account for 16% of the total cells in lung parenchyma have proliferation and secretion functions. Type II cells can synthesize and secrete pulmonary surfactant. The main components of the pulmonary surfactant are lipids (90%) and proteins (10%), and the proteins are specific pulmonary surfactant proteins (SPs). SPs have been named as SP-A, SP-B, SP-C, SP-D, based on the order of discovery, and SP-A was first discovered and has strong expression in pulmonary alveolar type II epithelial cells with abundant signals, and is rarely expressed in other tissues. Thus, SP-A is highly lung-specific, and is an ideal receptor in the lung tissue with specificity.

In addition to high affinity, an ideal targeting ligand should have a low molecular weight, high tissue penetration, and weak immunogenicity. Antigen-antibody binding is the strongest recognition mechanism, and therefore an antibody is the preferred ligand. However, although of high affinity, full antibodies are not ideal ligands due to their large molecular weight (with a relative molecular weight of 150,000), weak tissue penetration and strong immunogenicity. With the development of antibody and gene engineering technologies, antibody fragments (Fab, ScFv) now have the advantages of low molecular weight and weak immunogenicity, but they have lower stability and affinity than full antibodies.

In 1993, scientists from Belgium first reported the existence of Heavy Chain antibodies (HCAbs) without the light chain in the blood of camelids. The variable domain (VHH) of the heavy chains of HCAbs has a complete and independent antigen-binding capacity, and if cloned, a single domain antibodies in the nanometer scale which are known as Nanobodies® (Nbs) can be obtained. A nanobody has many advantages as a ligand: 1) small molecular weight, strong tissue penetration, and high affinity. It has a molecular weight of only 15,000 which is the lowest molecular weight among the known antibody molecules; its ability to penetrate tissues is significantly superior to full antibody, and its affinity with specific antigen is of nmol scale. 2) Stable structure. It can maintain stability even if stored at 37° C. for a week, under high temperature (90° C.), or under strong denaturing conditions such as being exposed to chaotropic agent, protease and strong pH value. 3) Weak immunogenicity. As its gene has high homology with human VH III family, it has weak immunogenicity and good biocompatibility. Because of these advantages, nanobodies have been studied extensively as new antibody drugs, but their use as targeted ligands for SP-A has not been reported.

SUMMARY OF THE INVENTION

The present invention provides a solution for the above-mentioned deficiencies of the prior art. The prior application CN104109207A discloses nanobodies that bind to rat's pulmonary surfactant protein A (SP-A)-, and the applicant continues to work on the nanobodies that bind to human pulmonary surfactant protein A (SP-A).

The present invention provides nanobodies that bind to human pulmonary surfactant protein A (SP-A) as well as the preparing methods and use of the same.

The present invention also provides nucleic acid encoding nanobodies that bind to pulmonary surfactant protein A.

The technical solutions are as follows:

In accordance with the first aspect of the present invention, a lung-targeting nanobody is provided. The nanobody comprises an amino acid sequence having the formula of $Q(x)_2 LVESGG(x)_2 V(x)_2 G(x) SL(x) LS(x)_{24} E(x)_{n2} KG(x)_4 S(x)_{n3} T(x)_2 Y(x) C(x)_{n4} S(x)_{n5} V(x)_{n6} R$; wherein x is any amino acid; n2~n6 are positive integers; $1 \leq n2 \leq 21$; $1 \leq n3 \leq 19$; $1 \leq n4 \leq 50$; $1 \leq n5 \leq 22$; $1 \leq n6 \leq 8$. Preferably, $17 \leq n2 \leq 21$; n3 is 18 or 19; $16 \leq n4 \leq 50$; $17 \leq n5 \leq 22$; n6 is 7 or 8.

In accordance with another embodiment of the present invention, the nanobody comprises an amino acid sequence having the formula of $Q(X_1) LVESGG(X_2) V(X_3) G(X_4) SL (X_5) LS(X_6) E(X_7) KG(X_8) S(X_9) T(X_{10}) Y(X_{11}) C(X_{12}) S(X_{13}) V(X_{14}) R$, wherein $X_1$ is selected from a group consisting of LQ (SEQ ID NO:16, 17, 18, 19, 20, 26, 30) and VK (SEQ ID NO:21, 22, 23, 24, 25, 27, 28, 29);

$X_2$ is selected from a group consisting of GS (SEQ ID NO:21, 22, 23, 24, 25, 27, 28, 29), GL (SEQ ID NO:16, 17, 18, 19, 20, 26, 30) and DL (SEQ ID NO:17);

$X_3$ is selected from a group consisting of QS (SEQ ID NO:30) and QP (SEQ ID NO:16, 18, 19, 20, 26);

$X_4$ is G (SEQ ID NO:16, 17, 18, 19, 20, 21, 22, 23, 24, 25, 26, 27, 28, 29, 30);

$X_5$ is selected from a group consisting of I (SEQ ID NO:28), S, R (SEQ ID NO:16, 18, 21, 22, 23, 24, 25, 26, 27, 29, 30) and T (SEQ ID NO:17);

$X_6$ is selected from a group consisting of

```
                         (SEQ ID NO:21,22,23,24,25,27,28,29)
CTASGSDYRWMYIARFRQCPGKER, (SEQ ID NO:16,26)
CAASEFTLDYYEIGWFRQAPGKDR, (SEQ ID NO:20)
CAASGFNLDDYADIGWFRQAPGKER, (SEQ ID NO:19)
CAVRGRDLDYYVIGWFRQAPGKER, (SEQ ID NO:18)
CTASKFHLDSYAVAWFRQTPGKER, (SEQ ID NO:30)
CAASGFTFNDYRMSWVRQAPGKGL
and (SEQ ID NO:17)
CTASGTFKIYSMGWYRRPQR;
```

$X_7$ is selected from a group consisting of

```
                         (SEQ ID NO:21,22,23,24,25,27,28,29)
GVAAIYTDDTDDSSPIYATSA, (SEQ ID NO:16,26)
GLSCIGYSDRIAYYSESV, (SEQ ID NO:20)
RVLCITISDGTTYYEDSG, (SEQ ID NO:19)
GVSCINNSDDTTYYSDSV, (SEQ ID NO:18)
AVSFINTSDDVTYFADSV, (SEQ ID NO:30)
WVSDINSGGSSTYYADSV
and (SEQ ID NO:17)
LVAEMLNGGDTQYSDSV;
```

$X_8$ is RFTIRFSIRFTV;

$X_9$ is selected from a group consisting of

```
                         (SEQ ID NO:21,22,23,24,25,27,28,29)
QDKDKNAVYLQMNSPKPED, (SEQ ID NO:16,26)
RDDATSTVSLYMDMMIPED, (SEQ ID NO:20)
TDIAKNTVFLQMDSLKAED, (SEQ ID NO:19)
RDHAKNTVYLQMNNLKPED, (SEQ ID NO:18)
RDNSKNTVYLQMNVLKPED, (SEQ ID NO:30)
RDNAKNTLYLQMNSLKPED
and (SEQ ID NO:17)
RTNNTMYLHMNNLKPED;
```

X10 is AMGTALSIAIAV;

$X_{11}$ is any amino acid or NULL;

$X_{12}$ is selected from a group consisting of

```
                         (SEQ ID NO:21,22,23,24,25,27,28,29)
AARAFGGTWSLSSPDDFSAWGQGTQVTVS, (SEQ ID NO:16,26)
AGSVVEPYELLPAAEYDYWGQGTRVTVS, (SEQ ID NO:20)
AGDPAPFCLYNTYVPRTWGQGTQVTVS, (SEQ ID NO:19)
AADFDRLDFTVKAMCVMKFFYYWGQGTQVTVS, (SEQ ID NO:18)
AAVRSPGPTGPSMQPMWSVPDLYDYWGQGTQVTVS, (SEQ ID NO:30)
VALLGRGCSGLVQGAFGPWGQGTQVTVS, (SEQ ID NO:17)
NLQDWYSEPAGDYWGPGTQVTVS;
```

$X_{13}$ is selected from a group consisting of

```
                         (SEQ ID NO:23,24,25,27,28,29)
GTNEVCKWPPRPCGRRCAGA, (SEQ ID NO:16,20,26,30)
AHHSEDPGPRGLAAAGAP
and (SEQ ID NO:17,18,19)
EPKTPKPQGPRGLAAAGAP;
```

$X_{14}$ is selected from a group consisting of (SEQ ID NO:21, 22, 23, 24, 25, 26, 27, 28, 29) and PYPDPLEP (SEQ ID NO:16, 17, 18, 19, 20, 26, 30).

Preferably, $X_{11}$ is Y, or V.

In accordance with another embodiment of the present invention, the nanobody comprises an amino acid sequence comprising any of SEQ ID NOs 16 to 30.

In accordance with the second aspect of the present invention, the present invention provides nucleic acids encoding the lung-targeting nanobody. Said nucleic acids encode the nanobody described in claim 1.

In accordance with an embodiment of the present invention, the nucleic acid comprise a polynucleotide sequence comprising any of SEQ ID NOs 1 to 15.

In accordance with the third aspect of the present invention, the present invention provides a method of preparing the antibody, comprising the steps of:

Step 1: fresh frozen human lung tissue sections were employed as antigen to screen the constructed nanobody library;

Step 2: selecting strains with high affinity with human pulmonary surfactant protein A and obtaining the relevant gene protein sequences;

Step 3: inducing the expression of the obtained gene sequences in Step 2.

In the method, preferably, the nanobody library in step 1 is pre-built anti pulmonary surfactant protein A nanobody libraries, by affinity selection.

Technical route of the method is shown in FIG. 9.

In accordance with the fourth aspect of the present invention, the present invention provides the use of nanobody as targeted ligand for SP-A.

In accordance with a preferred embodiment of the present invention, the specific target of the nanobodies is pulmonary surfactant protein A (SP-A).

SP-A was the first discovered pulmonary surfactant protein, has strong expression in pulmonary alveolar type II epithelial cells with abundant signals, and is rarely expressed in other tissues. SP-A is highly lung-specific, and is an ideal lung-specific receptor. In accordance with embodiments of the present invention, alpacas were immunized with SP-A, an antibody library was built, affinity selection was employed to screen and identify genes with lung-targeting specificity, and SP-A nanobodies with high affinity were obtained by prokaryotic expression. In vivo and in vitro experiments were conducted to verify the nanobody has high specificity for targeting lung tissue.

TABLE 1

| Abbreviation of amino acid | | |
|---|---|---|
| Full name | Abbreviation | Abbreviation |
| alanine | Ala | A |
| arginine | Arg | R |
| asparagine | Asn | N |
| aspartic acid | Asp | D |
| cysteine | Cys | C |
| glutanine | Gln | Q |
| glutamic acid | Glu | E |
| Glyicine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrosine | Tyr | Y |
| valine | Val | V |

Specifically, constructed anti pulmonary surfactant protein A (SP-A) nanobody library is incubated in fresh frozen sections of human lung, after several rounds of affinity selection, human lung tissue SP-A nanobody libraries is built, and 15 nanobodies strains which could bind human lung SP-A efficiently are screened out. Sequencing analysis showed they were all VHH sequences (nanobody sequences).

Nb4 had the highest affinity, and were selected as the preferred embodiments for prokaryotic expression to obtain nanobodies with a molecular weight of about 190,000 and a size of nanometer scale. In vitro Western Blot and ELISA experiments, Nb4 showed good affinity with hSP-A, immunohistochemistry and in vivo imaging results showed its lung-targeting specificity as it could bind to natural SP-A in the lung tissue.

In accordance to another embodiment of the present invention, synthetic method was used to obtain the polypeptide of the human lung tissue nanobody.

To further optimize the human lung tissue nanobody of the present invention, the active region of the polypeptide sequences of the selected clones were tested. Wherein the polypeptide of Nb4 (without the MQAQKAG part, SEQ ID NO:16) is obtained by synthetic method. Testing results showed that the functional polypeptides of Nb4 still have good lung-targeting distribution specificity after the removal of MQAQKAG.

The present invention provides human pulmonary surfactant protein A nanobody (hSPA-Nb) against the human pulmonary surfactant protein A (SP-A). And through a variety of methods are verified human lung tissue SPA-Nb prepared by the invention has a good lung-targeting distribution specificity. The operation flow of the present invention is shown in FIG. 8.

In accordance with embodiments of the present invention, the human lung tissue SPA-Nb coding sequence refers to the nucleotide sequence of the SPA-Nb polypeptide, such as the sequences from SEQ ID NO:16 to SEQ ID NO:30 and its degenerate sequence. The degenerate sequence refers to sequences from SEQ ID NO:16 to SEQ ID NO:30 wherein one or more codons were substituted.

Corresponding amino acid codon see FIG. 10.

The SPA-Nb coding sequences also include variants of SEQ ID NO:16 to SEQ ID NO:30 that encoding proteins with the same functions as SPA-Nb. Such variants include (but are not limited to): the deletion, insertion or substitution of a plurality (usually 1-90, preferably 1-60, more preferably 1-20, most preferably 1-10) of nucleotides, and the adding at the 5' and/or 3' end of a plurality of (typically less than 60, preferably less than 30, more preferably less than 10, the top for 5 or less) nucleotides.

Once the SPA-Nb coding sequence is obtained, large quantities of the recombinant sequences can be obtained. This is usually done by cloning the sequence into a vector, and transferring to the cells, then using conventional methods to isolate the sequences from the proliferated host cell.

In addition, the sequences can also be obtained by synthetic methods, as the length of the inhibitory factor of the nanobodies of the present invention is short. Typically, a number of small fragments can be synthesized first, and a long fragment can be formed by linking the small fragments.

In accordance with the present invention, various forms of vectors known in the art, such as those that are commercially available, can be used. For example, using a commercially available vector, the nucleotide sequence encoding the polypeptide of the invention can be operably linked to expression control sequence to form a protein expression vector.

As used herein, the term “operably linked” means the situation where part of the DNA sequence can affect the activity of other part of the DNA sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, “operably linked” means that the DNA sequences being linked are contiguous, and, in the case of a secretory leader, contiguous and in reading phase.

In accordance with embodiments of the present invention, the term “host cell” includes prokaryotic cells and eukaryotic cells. Examples of commonly used prokaryotic host cells include *Escherichia coli, Bacillus subtilis*, etc. Commonly used eukaryotic host cells include yeast cells, insect cells, and mammalian cells. Preferably, the host cell is a eukaryotic cells, such as CHO cells, COS cells and the like.

The antibodies of the present invention can be prepared by various techniques known to those skilled in the art. For example, total protein extracted from fresh human lung tissue serves as an antigen which verify antibody targeting and specificity. These fragments or functional regions can be prepared using recombinant or synthesized by synthetic peptide synthesizer. Antibodies that bind unmodified human lung SPA gene product could be produced by immunizing animals with gene products of prokaryotic cells (such as *E. Coli*); antibodies binding to post-translationally modified forms thereof can be acquired by immunizing animals with gene products produced by eukaryotic cells (e.g., yeast or insect cells).

The technical solution of the present invention has the following technical effects compared with the prior art:

The present invention provides nanobodies that bind to human pulmonary surfactant protein A (hSP-A) with specificity. The present invention take fresh frozen sections of lung as antigen, gene sequences with high affinity with hSP-A were obtained by constructing an SP-A antibody library and affinity selection, and nanobodies with high affinity and small molecule weight were obtained by induced expression of the gene sequences through a prokaryotic expression vector. Immunohistochemistry and in vivo imaging in nude mice showed the nanobodies have high specificity for targeting lung tissue. By providing nanobodies with lung-targeting specificity, the present invention provides tools for further research on lung-targeting ligands for targeted drug delivery for human lung diseases.

BRIEF DESCRIPTION OF THE DRAWINGS

FIG. 10 shows corresponding amino acid codons.

DETAILED DESCRIPTION

The present invention is further illustrated using the following embodiments, but any of the embodiments or its combinations thereof should not be construed as a limitation to the scope of the present invention.

Example 1. The Preparation of Human Pulmonary Surfactant Protein A (hSP-A)

1.1 the Preparation of Human Pulmonary Surfactant Protein A (hSP-A)

Grind 5 mg fresh human lung tissue with the mixture of protein lysate and PMSF in a tissue grinder for 3 min (60 HZ, 90S), centrifuged supernatant, measuring protein content (BCA).

Figure 1:
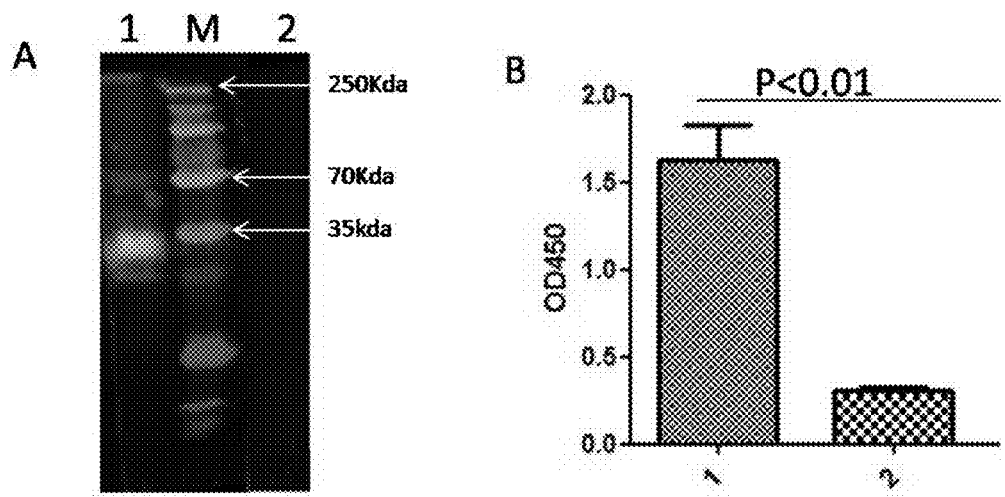
FIG. 1 shows Western blot and ELISA result of human pulmonary surfactant protein A (hSP-A); 1A is the result of Western blot for hSP-A (1: Mark, 2: hSP-A); 1B is the result of ELISA (1: hSP-A, 2: negative protein).

1.2 hSP-A Identification:

1.2.1 Western Blot:

Purified hSP-A was isolated by SDS-PAGE and transferred onto nitrocellulose membrane. It was sealed in 20% goat serum and incubated for 2 hours, then immune serum containing mouse polyclonal antibody against hSP-A (at room temperature for 2 hours, and washed 3 times with PBS) and serum containing anti-mouse IgG-HRP (at room temperature for 1 hours, washed 3 times with PBS) were added sequentially. Scanning of fluorescence scanner and photographs of the camera displays the target bands are around 35 Kd, 70 Kd, 120 Kd, multiple bands (FIG. 1A).

1.2.2 ELISA Test:

ELISA test was performed to measure the immunological activity of the purified protein. An ELISA plate with 96 wells were coated with purified hSP-A and an irrelevant protein, and incubated overnight at 4° C. The next day, it was sealed in 3% skim milk and incubated at 37° C. for an hour, then immune serum containing hSP-A monoclonal antibody (at room temperature for 2 hours, and washed 3 times with PBS) and serum containing goat anti-mouse IgG-HRP (at room temperature for 1 hours, washed 3 times with PBS) were added sequentially. TMB was added last to develop the image, and sulfuric acid was added to stop the reaction. The OD value of each well was measured using the chromogenic microplate, which showed that, compared with the control group, both purified hSP-A and SP-A monoclonal antibodies had obvious binding activity (FIG. 1B).

Example 2. Screening of hSPA-Specific Nanobody (rSPA-Nb)

Affinity selection technique was employed to screen the VHH antibody library with acetone fixed fresh frozen sections of human lung.

2.1 Simplified Procedure of Affinity Selection:

(1) fix fresh-frozen human lung slice with cold acetone for 30 min.

(2) wash the tubes 10 times using PBS, and dried by shaking.

(3) The tubes were blocked using 20% goat serum (1 ml serum was added in 4 ml PBS) and incubated for 2 hours at 37° C. The blocking solution was discarded, and the tubes were washed 3 times using PBS and dried.

(4) 200 μl of the prepared phage library was added to each fresh human lung slice, and incubated overnight at 4° C.

(5) The phage library on the slices was disposed, and the slices were washed three times with PBS, and dried.

(6) coat host strain TG1 which OD600 is 0.8200 μl on each slice, 37° C. 1 h, to wash away the bound phage library; wash with PBS 10 times, drying, scraping the tissue on the slide into 2YTAG, 3° C. until turbidity. This completed the first round of selection, and the first antibody library was obtained. The output of the antibody library was calculated.

(7) The selection steps were repeated for 3 times to obtain the third antibody library.

2.2 Preliminary Selection of Positive Nanobodies Using Indirect Phage ELISA.

(1) Single colonies obtained from the three rounds of selections and grown on 2YTAG plates were inoculated into the 96-well culture plate at 30° C., and cultured with shaking overnight.

(2) 300 ul of M13K07 helper phage was put in each well of another 96-well culture plate (labeled P1 Plate) the next day.
(3) 40 ul of cultured medium were taken from each well of the Master Plate, which was cultured overnight, and put in each well of the P1 Plate, and incubated at 37° C. with shaking overnight. The culture supernatant was prepared by centrifugation at 150 rpm for 20 minutes set aside, and the recombinant antibody was obtained.
(4) A 96-well microtiter plate was coated with hSP-A and incubated overnight at 4° C.
(5) 160 ul of recombinant antibody was mixed with 40 μL of MPBS, incubated for 20 minutes at room temperature. It was then added to blocked microtiter wells and incubated overnight at 4° C.
(6) Washing and adding HRP secondary antibody: HRP-labeled antibody against M13K07 was diluted 1:1000 in PBS, 200 ul of that was added to each well, and incubated and reacted for 1 hour at 37° C.
(7) 200 ul TMB substrate solution was added to each well, incubated at 37° C. for about 45 minutes to develop the image, 100 ul of stop solution was added to each well to stop the development process, and measurements were taken at 450 nm. Preliminary screening was conducted to select positive clones binding to hSP-A with specificity. If a clone has affinity value greater than 3 times the affinity value for the negative control great, then it is considered to be a positive clone.

Figure 2A:
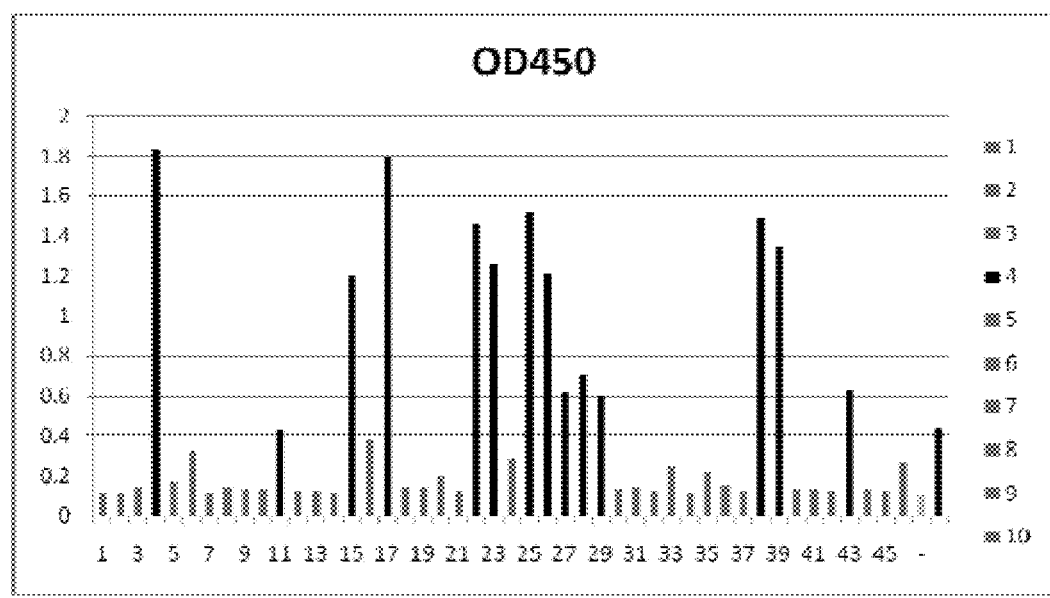
FIG. 2A is PHAGE-ELISA of affinity selection.
Figure 2B:
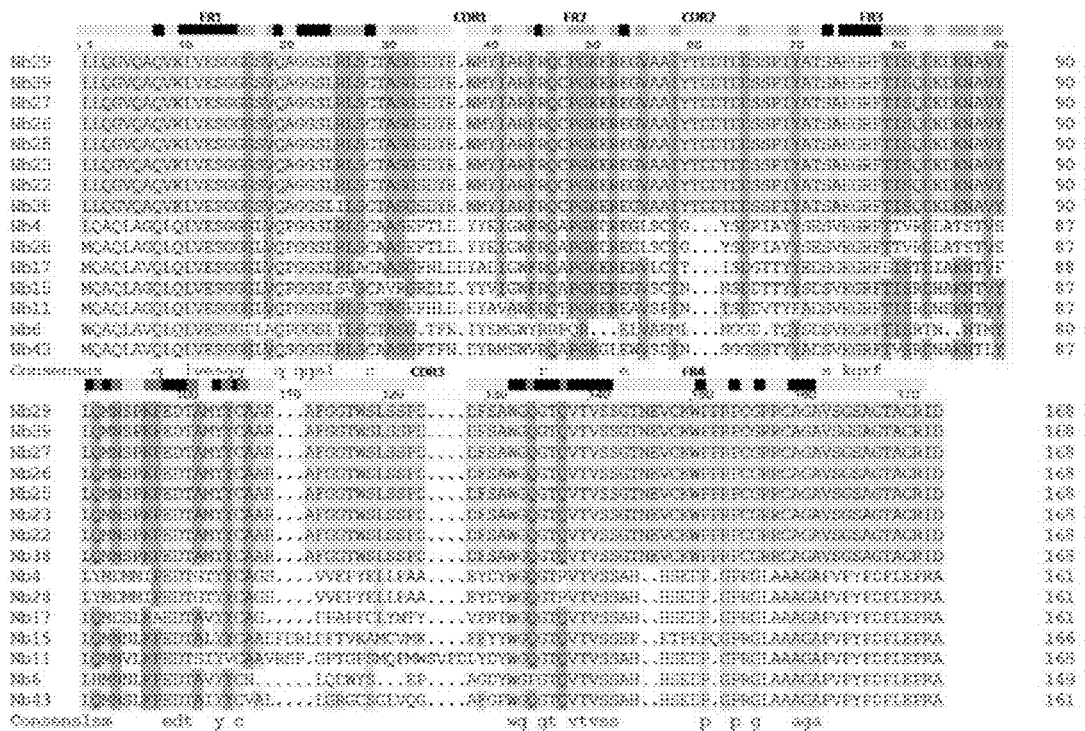
FIG. 2B is comparison of the coding sequences of the 15 clones.

Preliminary screening by indirect Phage ELISA showed that 15 sequences had affinity value greater three times the affinity value for the negative control group, and these 15 sequences were positive clones (FIG. 2).

Figure 3:
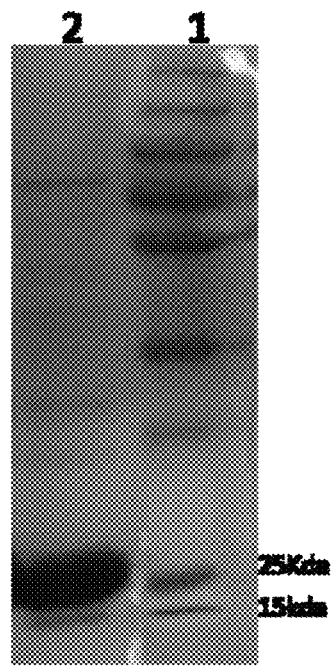
FIG. 3 is SDS-PAGE of human lung nanobody Nb4, (1: Mark, 2: Nb4).

Example 3. Expression and Purification of hSPA-Nb with Specificity 3.1 Construction of hSPA-Nb Prokaryotic Expression Vector The 15 clones selected by Phage ELISA were sent for sequencing (FIG. 3). No. 17 (Nb17) and No. 4 (Nb4) which had high affinity were PCR amplified using clone plasmid carrying BamH I and Xho I restriction sites. After the restriction digest, it was cloned to PET-26b (+) plasmid, and sent for sequencing.

3.2 Expression and Purification of Nanobodies

Figure 4:
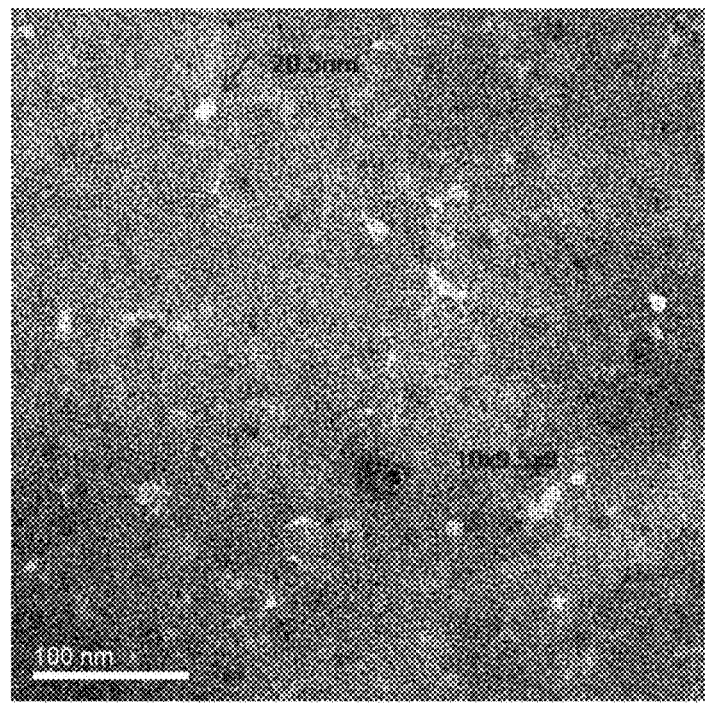
FIG. 4 is electron microscopy image of human lung tissue nanobodies Nb4.
Figure 5:
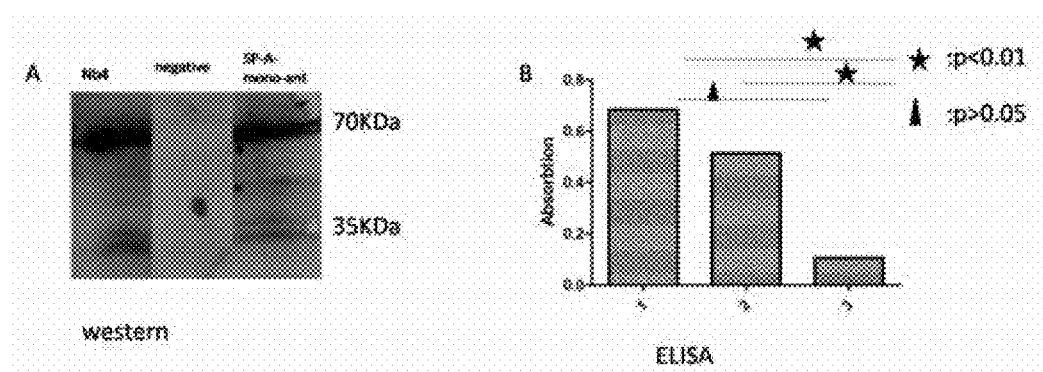
FIG. 5 shows the Western blot, ELISA results of purified SPA-Nb; wherein 5A for the Western blot (positive: SP-A-mono-ant, 17: Nb4, negative: H1N1 nanobodies); 5B for the ELISA test (−1: SP-A-mono-ant, 2: Nb4, 3: irrelevant nanobody); ★ represent P≤0.001, ▲ represent P>0.05.

Recombinant plasmid with correct sequence was transformed into *E. coli* BL21 (DE3), the expression conditions were optimized, and protein expression was induced at 25° C., 0.8 mmol/L IPTG. The expressed product was purified with nickel affinity chromatography and molecular sieve. SDS-PAGE electrophoresis showed that the expressed nanobody had a molecular weight of 19 kDa (FIG. 4). As measured by BCA, the purified proteins had concentration levels of 10 mg/L and 12 mg/L, respectively. Observed under the electron microscope, the size of the antibodies was in the nanometer scale. (FIG. 5).

The 15 clones obtained by the present invention are effective lung-targeting ligands as their nucleotide sequences and amino acid sequences specifically bind to SP-A, which are listed below:

1) Nucleotide sequence listing:

```
1) Nucleotide sequence listing:
NO. 1, Nb4 (SEQ ID NO 1):
TTGCAGGCCCAGCTGGCCGGTCAGTTGCAGCTCGTGGAGTCGGGGGGAGG

CTTGGTGCAGCCTGGGGGGTCTCTGAGACTCTCCTGTGCAGCCTCTGAAT

TCACTTTGGATTATTATGAAATAGGCTGGTTCCGGCAGGCCCCGGGGAAG

GACCGTGAGGGGCTCTCATGTATTGGTTATAGTGACAGAATCGCGTATTA

TTCAGAGTCCGTGAAGGGCCGATTCACCACCGTCAGAGACGACGCCACGA

GCACGGTCTCTCTTTATATGGATATGATGATTCCAGAGGACACAGGCACT

TATTATTGTGCGGGGTCGGTTGTGGAGCCTTACGAGTTACTGCCAGCGGC

TGAATATGACTACTGGGGACAGGGGACCCGGGTCACTGTCTCCTCAGCGC

ACCACAGCGAAGACCCCGGCCCCCGAGGCCTTGCGGCCGCAGGTGCGCCG

GTGCCGTATCCGGATCCGCTGGAACCGCGTGCCGCA;

NO. 2, Nb6 (SEQ ID NO 2):
TGGCAGGCCCAGCTGGCCGTTCAGTTGCAGCTCGTGGAGTCTGGGGGAGA

CTTGGCGCAGCCTGGGGGGTCTCTGACACTCTCCTGTACAGCCTCTGGAA

CGTTCAAGATCTATTCCATGGGCTGGTACCGCCGCCCTCAGCGCGAGTTG

GTCGCGGAAATGCTTAATGGTGGTGACACACAATATTCAGACTCCGTGAA

GGGCCGATTCACCATCTCCAGAACCAACAACACGATGTATCTCCACATGA

ACAACCTGAAACCTGAGGACACGGCCGTCTATTATTGTAATCTACAGGAT

TGGTATAGCGAACCTGCGGGCGACTATTGGGGCCCGGGGACCCAGGTCAC

CGTCTCCTCAGCGCACCACAGCGAAGACCCCGGCCCCCGAGGCCTTGCGG

CCGCAGGTGCGCCGGTGCCGTATCCGGATCCGCTGGAACCGCGTGCCGC

A;
```

-continued

NO. 3, Nb11 (SEQ ID NO 3):
ATGCAGGCCCAGCTGGCCGGTCAGTTGCAGCTCGTGGAGTCTGGGGGAGG

CTTGGTGCAGCCTGGGGGGTCTCTGAGACTCTCCTGTACAGCCTCTAAAT

TCCATTTGGATTCTTATGCCGTAGCCTGGTTCCGCCAGACCCCAGGGAAG

GAGCGTGAGGCGGTCTCATTTATAAATACTAGTGATGATGTCACATACTT

TGCTGACTCCGTAAAGGGCCGATTCACCATCTCCAGAGACAACTCCAAGA

ACACGGTATATCTGCAAATGAACGTCCTGAAACCAGAAGACACTTCTATT

TATGTGTGTGCAGCGGTAAGAAGTCCCGGCCCTACCGGCCCTAGTATGCA

GCCTATGTGGTCGGTGCCTGACCTGTATGACTACTGGGGCCAGGGGACCC

AGGTCACCGTCTCCTCAGCGCACCACAGCGAAGACCCCGGCCCCCGAGGC

CTTGCGGCCGCAGGTGCGCCGGTGCCGTATCCGGATCCGCTGGAACCGCG

TGCCGCA;

NO. 4, Nb15 (SEQ ID NO 4):
ATGCAGGCCCAGCTGGCCGGTCAGTTGCAGCTCGTGGAGTCTGGGGGAGG

CTTGGTGCAGCCTGGGGGGTCTCTGAGCGTCTCCTGCGCAGTCCGAGGAC

GCGATTTGGATTATTATGTCATCGGTTGGTTCCGCCAGGCCCCAGGGAAG

GAGCGTGAGGGTGTTTCATGCATTAATAATAGTGATGATACCACATACTA

TTCAGACTCCGTGAAGGGCCGATTTACCATCTCGAGAGATCACGCCAAGA

ACACGGTATATCTCCAAATGAACAACCTGAAACCTGAGGACACCGCCCTT

TATTACTGTGCAGCGGATTTCGATCGCCTCGATTTTACTGTTAAGGCTAT

GTGTGTTATGAAGTTCTTTTACTACTGGGGCCAGGGGACGCAGGTCACCG

TCTCCTCAGAACCCAAGACACCAAAACCACAAGGCCCCCGAGGCCTTGCG

GCCGCAGGTGCGCCGGTGCCGTATCCGGATCCGCTGGAACCGCGTGCCGC

A;

NO. 5, Nb17 (SEQ ID NO 5):
ATGCAGGCCCAGCTGGCCGTTCAGTTGCAGCTCGTGGAGTCAGGTGGAGG

CTTGGTGCAGCCTGGGGGGTCTCTGAGACTCGCCTGTGCAGCTTCTGGAT

TCAATTTGGATGATTATGCAGACATAGGCTGGTTCCGCCAGGCCCCAGGG

AAGGAGCGTGAACGAGTCCTTTGTATTACTATTAGTGATGGTACCACATA

CTATGAAGACTCCGGGAAGGGCCGATTCTCCATCTCCACAGACATCGCCA

AGAACACGGTGTTTCTTCAAATGGACAGCCTGAAAGCTGAGGACACAGCC

GTTTATTATTGTGCAGGAGATCCCGCCCCTTTTTGTCTCTATAACACCTA

TGTACCGCGAACCTGGGCCAGGGGACCCAGGTCACCGTCTCCTCGGCGC

ACCACAGCGAAGACCCCGGCCCCCGAGGCCTTGCGGCCGCAGGTGCGCCG

GTGCCGTATCCGGATCCGCTGGAACCGCGTGCCGCA;

NO. 6, Nb22 (SEQ ID NO 6):
CTCTTCTACAAGGTGTCCAGGCTCAGGTGAAGCTGGTGGAGTCTGGGGGA

GGCTCGGTGCAGGCTGGAGGGTCTCTGAGACTCTCCTGTACAGCCTCTGG

ATCAGACTACAGATGGATGTACATCGCCCGGTTTCGCCAATGTCCAGGGA

AGGAGCGCGAGGGGGTCGCAGCAATTTATACTGATGATACTGATGATAGT

AGTCCGATCTATGCCACCTCCGCCAAGGGCCGATTCACCATCTCCCAAGA

CAAGGACAAGAACGCGGTATATCTGCAAATGAACAGCCCGAAACCTGAGG

ACACTGCCATGTACTACTGTGCGGCAAGAGCGTTCGGTGGTACCTGGAGC

-continued

TTGAGCTCCCCGGACGACTTTAGTGCCTGGGGCCAGGGGACCCAGGTCAC
CGTCTCCTCAGGAACGAATGAAGTATGCAAGTGGCCCCCGAGGCCTTGCG
GCCGCAGGTGCGCCGGTGCCGTATCCGGATCCGCTGGAACCGCGTGCCGC
ATAGACTGT;

NO. 7, Nb23 (SEQ ID NO 7):
TCTTCTACAAGGTGTCCAGGCTCAGGTGAAGCTGGTGGAGTCTGGGGGAG
GCTCGGTGCAGGCTGGAGGGTCTCTGAGACTCTCCTGTACAGCCTCTGGA
TCAGACTACAGATGGATGTACATCGCCCGGTTTCGCCAATGTCCAGGGAA
GGAGCGCGAGGGGGTCGCAGCAATTTATACTGATGATACTGATGATAGTA
GTCCGATCTATGCCACCTCCGCCAAGGGCCGATTCACCATCTCCCAAGAC
AAGGACAAGAACGCGGTATATCTGCAAATGAACAGCCCGAAACCTGAGGA
CACTGCCATGTACTACTGTGCGGCAAGAGCGTTCGGTGGTACCTGGAGCT
TGAGCTCCCCGGACGACTTTAGTGCCTGGGGCCAGGGGACCCAGGTCACC
GTCTCCTCAGGAACGAATGAAGTATGCAAGTGGCCCCCGAGGCCTTGCGG
CCGCAGGTGCGCCGGTGCCGTATCCGGATCCGCTGGAACCGCGTGCCGC
A;

NO. 8, Nb25 (SEQ ID NO 8):
TGCTCTTCTACAAGGTGTCCAGGCTCAGGTGAAGCTGGTGGAGTCTGGGG
GAGGCTCGGTGCAGGCTGGAGGGTCTCTGAGACTCTCCTGTACAGCCTCT
GGATCAGACTACAGATGGATGTACATCGCCCGGTTTCGCCAATGTCCAGG
GAAGGAGCGCGAGGGGGTCGCAGCAATTTATACTGATGATACTGATGATA
GTAGTCCGATCTATGCCACCTCCGCCAAGGGCCGATTCACCATCTCCCAA
GACAAGGACAAGAACGCGGTATATCTGCAAATGAACAGCCCGAAACCTGA
GGACACTGCCATGTACTACTGTGCGGCAAGAGCGTTCGGTGGTACCTGGA
GCTTGAGCTCCCCGGACGACTTTAGTGCCTGGGGCCAGGGGACCCAGGTC
ACCGTCTCCTCAGGAACGAATGAAGTATGCAAGTGGCCCCCGAGGCCTTG
CGGCCGCAGGTGCGCCGGTGCCGTATCCGGATCCGCTGGAACCGCGTGCC
GCA;

NO. 9, Nb26 (SEQ ID NO 9):
TCTTCTACAAGGTGTCCAGGCTCAGGTGAAGCTGGTGGAGTCTGGGGGAG
GCTCGGTGCAGGCTGGAGGGTCTCTGAGACTCTCCTGTACAGCCTCTGGA
TCAGACTACAGATGGATGTACATCGCCCGGTTTCGCCAATGTCCAGGGAA
GGAGCGCGAGGGGGTCGCAGCAATTTATACTGATGATACTGATGATAGTA
GTCCGATCTATGCCACCTCCGCCAAGGGCCGATTCACCATCTCCCAAGAC
AAGGACAAGAACGCGGTATATCTGCAAATGAACAGCCCGAAACCTGAGGA
CACTGCCATGTACTACTGTGCGGCAAGAGCGTTCGGTGGTACCTGGAGCT
TGAGCTCCCCGGACGACTTTAGTGCCTGGGGCCAGGGGACCCAGGTCACC
GTCTCCTCAGGAACGAATGAAGTATGCAAGTGGCCCCCGAGGCCTTGCGG
CCGCAGGTGCGCCGGTGCCGTATCCGGATCCGCTGGAACCGCGTGCCGCA
TAGACTGT;

NO. 10, Nb27 (SEQ ID NO 10):
TCTTCTACAAGGTGTCCAGGCTCAGGTGAAGCTGGTGGAGTCTGGGGGAG

GCTCGGTGCAGGCTGGAGGGTCTCTGAGACTCTCCTGTACAGCCTCTGGA

TCAGACTACAGATGGATGTACATCGCCCGGTTTCGCCAATGTCCAGGGAA

GGAGCGCGAGGGGGTCGCAGCAATTTATACTGATGATACTGATGATAGTA

GTCCGATCTATGCCACCTCCGCCAAGGGCCGATTCACCATCTCCCAAGAC

AAGGACAAGAACGCGGTATATCTGCAAATGAACAGCCCGAAACCTGAGGA

CACTGCCATGTACTACTGTGCGGCAAGAGCGTTCGGTGGTACCTGGAGCT

TGAGCTCCCCGGACGACTTTAGTGCCTGGGGCCAGGGGACCCAGGTCACC

GTCTCCTCAGGAACGAATGAAGTATGCAAGTGGCCCCCGAGGCCTTGCGG

CCGCAGGTGCGCCGGTGCCGTATCCGGATCCGCTGGAACCGCGTGCCGCA

TAGACTGT;

NO. 11, Nb28 (SEQ ID NO 11):
ATGCAGGCCCAGCTGGCCGGTCAGTTGCAGCTCGTGGAGTCGGGGGGAGG

CTTGGTGCAGCCTGGGGGGTCTCTGAGACTCTCCTGTGCAGCCTCTGAAT

TCACTTTGGATTATTATGAAATAGGCTGGTTCCGGCAGGCCCCGGGGAAG

GACCGTGAGGGGCTCTCATGTATTGGTTATAGTGACAGAATCGCGTATTA

TTCAGAGTCCGTGAAGGGCCGATTCACCACCGTCAGAGACGACGCCACGA

GCACGGTCTCTCTTTATATGGATATGATGATTCCAGAGGACACAGGCACT

TATTATTGTGCGGGGTCGGTTGTGGAGCCTTACGAGTTACTGCCAGCGGC

TGAATATGACTACTGGGGACAGGGGACCCGGGTCACTGTCTCCTCAGCGC

ACCACAGCGAAGACCCCGGCCCCCGAGGCCTTGCGGCCGCAGGTGCGCCG

GTGCCGTATCCGGATCCGCTGGAACCGCGTGCCGCA;

NO. 12, Nb29 (SEQ ID NO 12):
TCTTCTACAAGGTGTCCAGGCTCAGGTGAAGCTGGTGGAGTCTGGGGGAG

GCTCGGTGCAGGCTGGAGGGTCTCTGAGACTCTCCTGTACAGCCTCTGGA

TCAGACTACAGATGGATGTACATCGCCCGGTTTCGCCAATGTCCAGGGAA

GGAGCGCGAGGGGGTCGCAGCAATTTATACTGATGATACTGATGATAGTA

GTCCGATCTATGCCACCTCCGCCAAGGGCCGATTCACCATCTCCCAAGAC

AAGGACAAGAACGCGGTATATCTGCAAATGAACAGCCCGAAACCTGAGGA

CACTGCCATGTACTACTGTGCGGCAAGAGCGTTCGGTGGTACCTGGAGCT

TGAGCTCCCCGGACGACTTTAGTGCCTGGGGCCAGGGGACCCAGGTCACC

GTCTCCTCAGGAACGAATGAAGTATGCAAGTGGCCCCCGAGGCCTTGCGG

CCGCAGGTGCGCCGGTGCCGTATCCGGATCCGCTGGAACCGCGTGCCGC

A;

NO. 13, Nb38 (SEQ ID NO 13):
TCTTCTACAAGGTGTCCAGGCTCAGGTGAAGCTGGTGGAGTCTGGGGGAG

GCTCGGTGCAGGCTGGAGGGTCTCTGATACTCTCCTGTACAGCCTCTGGA

TCAGACTACAGATGGATGTACATCGCCCGGTTTCGCCAATGTCCAGGGAA

GGAGCGCGAGGGGGTCGCAGCAATTTATACTGATGATACTGATGATAGTA

GTCCGATCTATGCCACCTCCGCCAAGGGCCGATTCACCATCTCCCAAGAC

AAGGACAAGAACGCGGTATATCTGCAAATGAACAGCCCGAAACCTGAGGA

-continued
CACTGCCATGTACTACTGTGCGGCAAGAGCGTTCGGTGGTACCTGGAGCT

TGAGCTCCCCGGACGACTTTAGTGCCTGGGGCCAGGGGACCCAGGTCACC

GTCTCCTCAGGAACGAATGAAGTATGCAAGTGGCCCCCGAGGCCTTGCGG

CCGCAGGTGCGCCGGTGCCGTATCCGGATCCGCTGGAACCGCGTGCCGC

A;

NO. 14, Nb39 (SEQ ID NO 14):
TCTTCTACAAGGTGTCCAGGCTCAGGTGAAGCTGGTGGAGTCTGGGGGAG

GCTCGGTGCAGGCTGGAGGGTCTCTGAGACTCTCCTGTACAGCCTCTGGA

TCAGACTACAGATGGATGTACATCGCCCGGTTTCGCCAATGTCCAGGGAA

GGAGCGCGAGGGGGTCGCAGCAATTTATACTGATGATACTGATGATAGTA

GTCCGATCTATGCCACCTCCGCCAAGGGCCGATTCACCATCTCCCAAGAC

AAGGACAAGAACGCGGTATATCTGCAAATGAACAGCCCGAAACCTGAGGA

CACTGCCATGTACTACTGTGCGGCAAGAGCGTTCGGTGGTACCTGGAGCT

TGAGCTCCCCGGACGACTTTAGTGCCTGGGGCCAGGGGACCCAGGTCACC

GTCTCCTCAGGAACGAATGAAGTATGCAAGTGGCCCCCGAGGCCTTGCGG

CCGCAGGTGCGCCGGTGCCGTATCCGGATCCGCTGGAACCGCGTGCCGC

A;

NO. 15, Nb43 (SEQ ID NO 15):
ATGCAGGCCCAGCTGGCCGTTCAGTTGCAGCTCGTGGAGTCGGGGGGAGG

CTTGGTGCAATCTGGGGGGTCTCTGAGACTCTCCTGTGCAGCCTCTGGAT

TCACTTTCAATGACTATCGCATGAGCTGGGTCCGCCAGGCTCCAGGAAAG

GGGCTCGAGTGGGTCTCAGATATTAACAGTGGTGGTAGTAGTACATACTA

TGCAGACTCCGTGAAGGGCCGATTCACCGTCTCCAGAGACAACGCCAAGA

ACACGCTGTATCTGCAAATGAACAGCCTGAAACCTGAGGACACGGCCATT

TACTACTGTGTGGCCCTACTTGGGCGCGGTTGTTCAGGCTTGGTTCAGGG

GGCCTTTGGACCCTGGGGCCAGGGGACCCAGGTCACCGTCTCCTCGGCGC

ACCACAGCGAAGACCCCGGCCCCCGAGGCCTTGCGGCCGCAGGTGCGCCG

GTGCCGTATCCGGATCCGCTGGAACCGCGTGCCGCA;

2) Amino acid sequence listing:
NO. 16, Nb4 (SEQ ID NO 16):
  1  LQAQLAGQLQ LVESGGGLVQ PGGSLRLSCA ASEFTLDYYE IGWFRQAPGK DREGLSCIGY
 61  SDRIAYYSES VKGRFTTVRD DATSTVSLYM DMMIPEDTGT YYCAGSVVEP YELLPAAEYD
121  YWGQGTRVTV SSAHHSEDPG PRGLAAAGAP VPYPDPLEPR AA;

NO. 17, Nb6 (SEQ ID NO 17):
  1  WQAQLAVQLQ LVESGGDLAQ PGGSLTLSCT ASGTFKIYSM GWYRRPQREL VAEMLNGGDT
 61  QYSDSVKGRF TISRTNNTMY LHMNNLKPED TAVYYCNLQD WYSEPAGDYW GPGTQVTVSS
121  AHHSEDPGPR GLAAAGAPVP YPDPLEPRAA;

NO. 18, Nb11 (SEQ ID NO 18):
  1  MQAQLAGQLQ LVESGGGLVQ PGGSLRLSCT ASKFHLDSYA VAWFRQTPGK EREAVSFINT
 61  SDDVTYFADS VKGRFTISRD NSKNTVYLQM NVLKPEDTSI YVCAAVRSPG PTGPSMQPMW
121  VPDLYDYWGQ GTQVTVSSAH HSEDPGPRGL AAAGAPVPYP DPLEPRAA

NO. 19, Nb15 (SEQ ID NO 19):
  1  MQAQLAGQLQ LVESGGGLVQ PGGSLSVSCA VRGRDLDYYV IGWFRQAPGK EREGVSCINN
 61  SDDTTYYSDS VKGRFTISRD HAKNTVYLQM NNLKPEDTAL YYCAADFDRL DFTVKAMCVM
121  KFFYYWGQGT QVTVSSEP KTPKPQGPRG LAAAGAPVPY PDLEPRAA;

NO. 20, Nb17 (SEQ ID NO 20):
  1  MQAQLAVQLQ LVESGGGLVQ PGGSLRLACA ASGFNLDDYA DIGWFRQAPG KERERVLCIT
 61  ISDGTTYYED SGKGRFSIST DIAKNTVFLQ MDSLKAEDTA VYYCAGDPAP FCLYNTYVPR
121  TWGQGTQVTV SSAHHSEDPG PRGLAAAGAP VPYPDPLEPRAA;

-continued

```
NO. 21, Nb22 (SEQ ID NO 21):
  1    LLQGVQAQVK LVESGGGSVQ AGGSLRLSCT ASGSDYRWMY IARFRQCPGK EREGVAAIY
 61    TDDTDDSSPI YATSAKGRFT ISQDKDKNAV YLQMNSPKPE DTAMYYCAAR AFGGTWSLSS
121    PDDFSAWGQG TQVTVSSGTN EVCKWPPRPC GRRCAGAVSG SAGTACRIDC

NO. 22, Nb23 (SEQ ID NO 22):
  1    LLQGVQAQVK LVESGGGSVQ AGGSLRLSCT ASGSDYRWMY IARFRQCPGK EREGVAAIYT
 61    DDTDDSSPIY ATSAKGRFTI SQDKDKNAVY LQMNSPKPED TAMYYCAARA FGGTWSLSSP
121    DDFSAWGQGT QVTVSSGTNE VCKWPPRPCG RRCAGAVSGS AGTACRIDC

NO. 23, Nb25 (SEQ ID NO 23):
  1    ALLQGVQAQV KLVESGGGSV QAGGSLRLSC TASGSDYRWM YIARFRQCPG KEREGVAAIY
 61    TDDTDDSSPI YATSAKGRFT ISQDKDKNAV YLQMNSPKPE DTAMYYCAAR AFGGTWSLSS
121    PDDFSAWGQG TQVTVSSGTN EVCKWPPRPC GRRCAGAVSG SAGTACRIDC

NO. 24, Nb26 (SEQ ID NO 24):
  1    LLQGVQAQVK LVESGGGSVQ AGGSLRLSCT ASGSDYRWMY IARFRQCPGK EREGVAAIYT
 61    DDTDDSSPIY ATSAKGRFTI SQDKDKNAVY LQMNSPKPED TAMYYCAARA FGGTWSLSSP
121    DDFSAWGQGT QVTVSSGTNE VCKWPPRPCG RRCAGAVSGS AGTACRIDC

NO. 25, Nb27 (SEQ ID NO 25):
  1    LLQGVQAQVK LVESGGGSVQ AGGSLRLSCT ASGSDYRWMY IARFRQCPGK EREGVAAIYT
 61    DDTDDSSPIY ATSAKGRFTI SQDKDKNAVY LQMNSPKPED TAMYYCAARA FGGTWSLSSP
121    DDFSAWGQGT QVTVSSGTNE VCKWPPRPCG RRCAGAVSGS AGTACRIDC

NO. 26, Nb28 (SEQ ID NO 26):
  1    MQAQLAGQLQ LVESGGGLVQ PGGSLRLSCA ASEFTLDYYE IGWFRQAPGK DREGLSCIGY
 61    SDRIAYYSES VKGRFTTVRD DATSTVSLYM DMMIPEDTGT YYCAGSVVEP YELLPAAEYD
121    YWGQGTRVTV SSAHHSEDPG PRGLAAAGAP VPYPDPLEPR AA;

NO. 27, Nb29 (SEQ ID NO 27):
  1    LLQGVQAQVK LVESGGGSVQ AGGSLRLSCT ASGSDYRWMY IARFRQCPGK EREGVAAIYT
 61    DDTDDSSPIY ATSAKGRFTI SQDKDKNAVY LQMNSPKPED TAMYYCAARA FGGTWSLSSP
121    DDFSAWGQGT QVTVSSGTNE VCKWPPRPCG RRCAGAVSGS AGTACRIDC

NO. 28, Nb38 (SEQ ID NO 28):
  1    LLQGVQAQVK LVESGGGSVQ AGGSLILSCT ASGSDYRWMY IARFRQCPGK EREGVAAIYT
 61    DDTDDSSPIY ATSAKGRFTI SQDKDKNAVY LQMNSPKPED TAMYYCAARA FGGTWSLSSP
121    DDFSAWGQGT QVTVSSGTNE VCKWPPRPCG RRCAGAVSGS AGTACRIDC

NO. 29, Nb39 (SEQ ID NO 29):
  1    LLQGVQAQVK LVESGGGSVQ AGGSLRLSCT ASGSDYRWMY IARFRQCPGK EREGVAAIYT
 61    DDTDDSSPIY ATSAKGRFTI SQDKDKNAVY LQMNSPKPED TAMYYCAARA FGGTWSLSSP
121    DDFSAWGQGT QVTVSSGTNE VCKWPPRPCG RRCAGAVSGS AGTACRIDC

NO. 30, Nb43 (SEQ ID NO 30):
  1    MQAQLAVQLQ LVESGGGLVQ SGGSLRLSCA ASGFTFNDYR MSWVRQAPGK GLEWVSDINS
 61    GGSSTYYADS VKGRFTVSRD NAKNTLYLQM NSLKPEDTAI YYCVALLGRG CSGLVQGAFG
121    PWGQGTQVTV SSAHHSEDPG PRGLAAAGAP VPYPDPLEPR AA.
```

Example 4. Testing of hSPA-Nb's Lung-Specificity

To further verify the affinity between hSPA-Nb and human pulmonary surfactant protein A, and whether hSPA-Nb has lung-specificity, Western blot and ELISA were used to preliminarily measure the antigen specificity of hSPA-Nb, and immunohistochemistry and in vivo imaging were used to verify its lung-specificity in vivo.

4.1 Western Blot and ELISA

Figure 6:
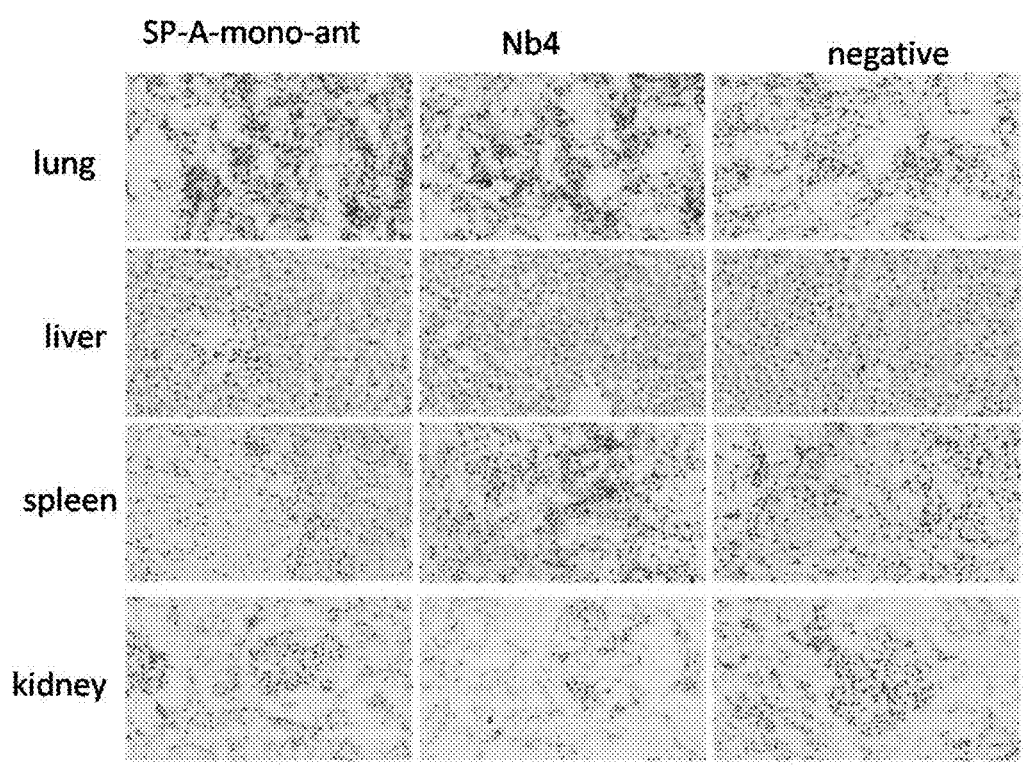
FIG. 6 is immunostaining result of human lung tissue nanobody Nb4 with sliced tissues of human lung, heart, liver, spleen, muscle.

Purified human lung tissue SPA-Nb4, irrelevant nanobody (H1N1 nanobodies) and commercial anti-human SP-A monoclonal antibody were selected as the primary antibody to test the affinity between SPA-Nb4 and hSPA using Western blot and ELISA (using the same method described in section 1.2). The results showed that Nb4 had significant binding specificity with hSPA (FIG. 6A, 6B).

4.2 Cell Immunofluorescence

Figure 7:
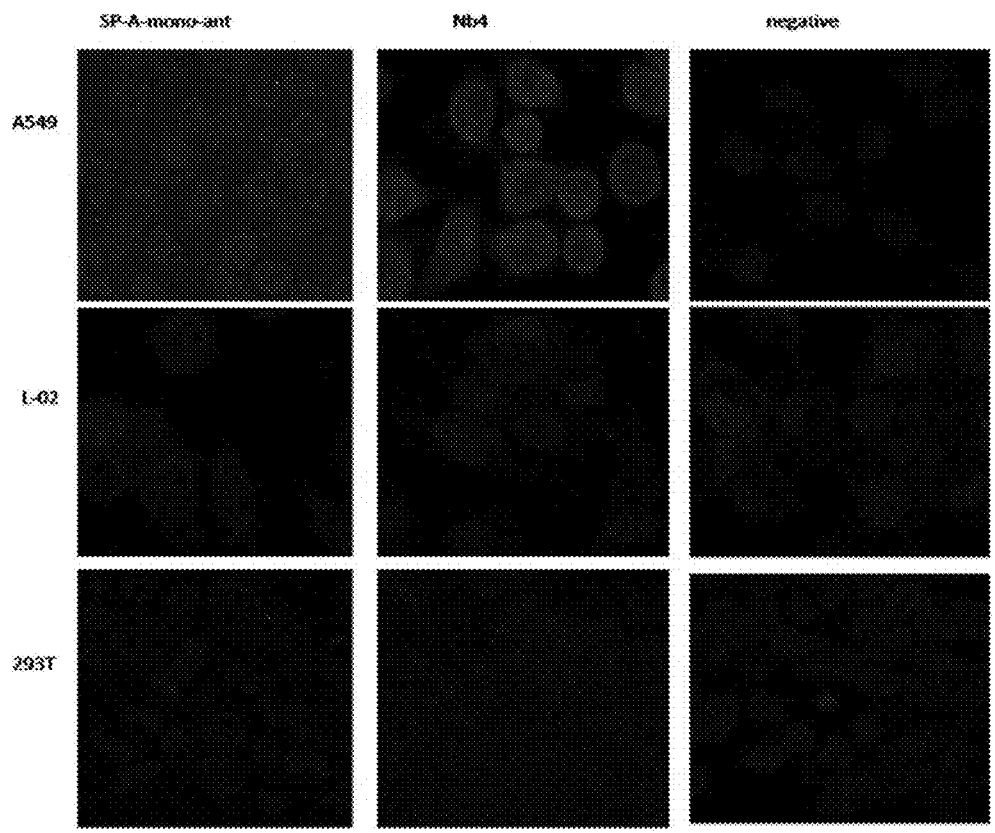
FIG. 7 shows cell immunofluorescence result of human lung tissue nanobodies Nb4 with A549, L-02,293T cells.

When A549 (lung), L-02 (liver), 293T (kidney) cells were grown and cover the cell plates to 95%-100%, PBS washed 3 times, incubated in fixative 30 min, PBS washed 3 times, 0.2% Triton X-100 permeabilization 5 min, blocked for 1 h by 20% goat serum, diluted primary antibody (human lung tissues Nb4-Fitc) for the experimental group, anti-human SP-A monoclonal antibody as a positive control group, and H1N1-Fitc nanobodies as a negative control group) was dropped on. The secondary antibody was anti-mouse-IgG-APC. The results showed that Nb4 and SPA monoclonal antibody (SPA-monopoly-ant) had significant binding effect with human lung tissue (shown as green/red), wherein the human lung tissue Nb4 binding ability is similar with SPA-monopoly-ant. All three antibodies had no obvious binding effect with human heart, liver, spleen, kidney, muscle tissues, nor had the negative control group (FIG. 7).

4.3 Immunohistochemistry

Figure 8:
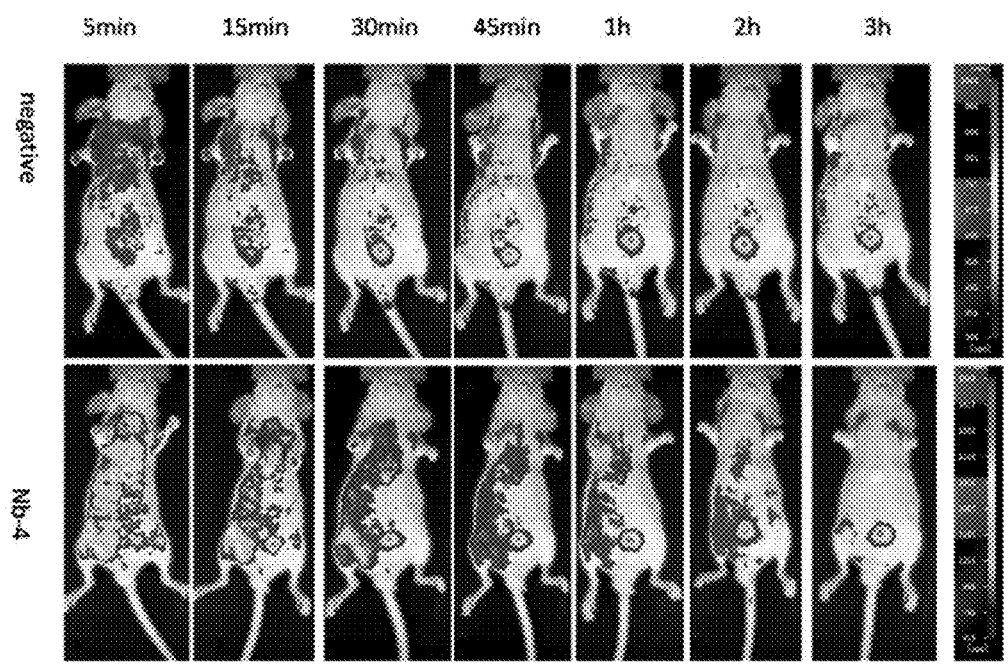
FIG. 8 shows images of human lung tissue nanobodies Nb4 with FITC mark in the body of nude mouse at different times (respectively: after intravenous injection of 5 min, 15 min, 30 min, 45 min, 1 h, 1.5 h, 2 h, 3 h).

The fresh human lung, liver, spleen, kidney and other tissue sections were fixed, diluted primary antibody (human lung tissues Nb4 for the experimental group, SP-A monoclonal antibody as a positive control group, and H1N1 nanobodies as a negative control group) was dropped on. The secondary antibody was His-IgG-HRP or anti-mouse-IgG-HRP. The results showed that human lung tissues Nb4 and SPA monoclonal antibody (SPA-monopoly-ant) had significant binding effect with human lung tissue (shown as brown), wherein Nb4 binding ability is similar with SPA-monopoly-ant. All three antibodies had no obvious binding effect with human heart, liver, spleen, kidney, muscle tissues, nor had the negative control group (FIG. 8).

4.4 In Vivo Lung-Specificity Testing Using FITC-Marked Nanobody in Mice

Figure 9:
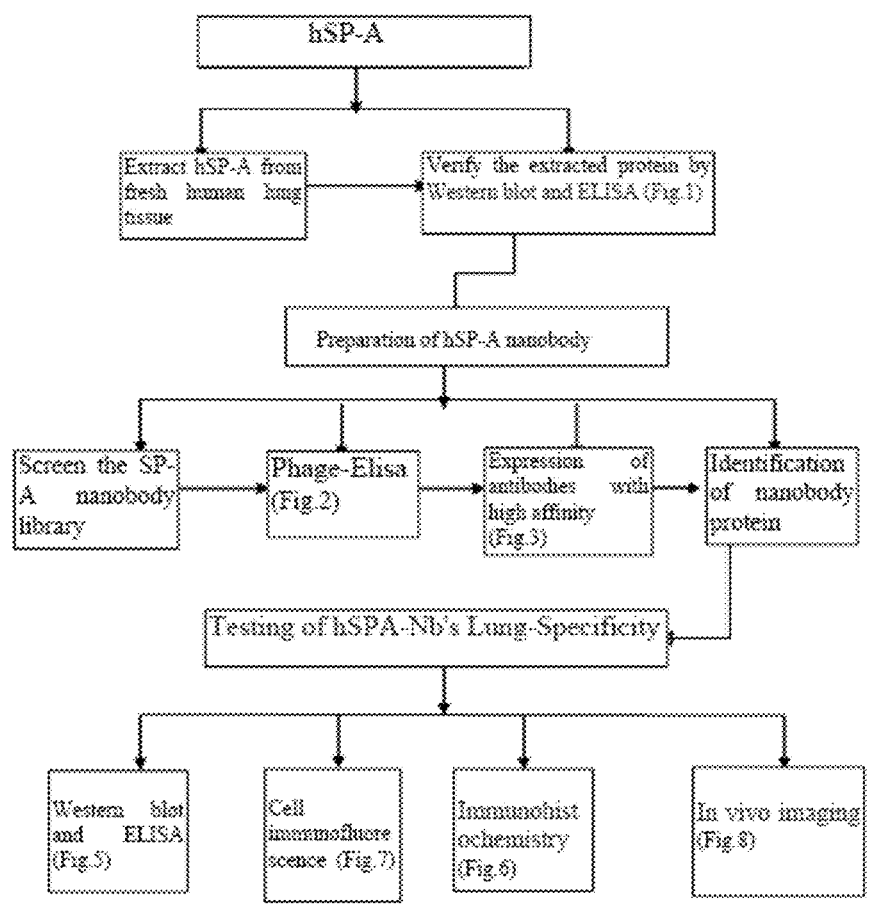
FIG. 9 shows the preparation process of human lung tissue hSPA-Nb.

Sequence homology analysis showed that there is a high degree of homology between the amino acid sequence of human and mouse rSPA. Since it is easier to obtain in vivo imaging using nude mice, nude mice were chosen for testing specificity in vivo. Five-week-old nude mice were chosen, and after continuous inhalation anesthesia, 200 ul FITC-labeled nanobody was injected intravenously at the tail, and the dose was 1 mg/kg of the animal body weight. The nude mice were imaged at 5 minutes, 15 minutes, 30 minutes, 45 minutes, 1 hour, 2 hours, 3 hours after the injection, respectively. At the same time, 200 ul H1N1-Fitc nanobody was injected intravenously at the tail as the negative control group (FIG. 9). The results showed that 15 minutes after intravenous injection, the FITC-labeled nanobody began to clearly cluster in the lung. 2 hours after the injection, the clustering in the lung was still obvious, and the lung-targeting effect was similar to that of the nasal inhalation.

The above experiment was repeated using the functional region of the polypeptides of synthetic human lung tissues Nb4 (SEQ ID NO:16 and Nb17 (SEQ ID NO:20) (without the MQAQKAG portion). It was found that the synthetic polypeptides also bound to hSPA with specificity, and clustered around the lung in vivo testing.

Example 5. Clone Protein Expression and Targeting Detection

Sequence homology comparative analysis was conducted on the selected 15 sequences, and it was found that human lung tissues Nb23, Nb25, Nb27, Nb29 and Nb39 had the same polypeptide sequence, human lung tissues Nb28 and Nb4 had high sequence similarity; while the rest of the sequences were quite different.

To further verify that the 15 nanobody sequences exhibits lung-targeting affinity with SP-A, 8 clones (excluding those with the same sequence as Nb4) were expressed and purified in accordance with the method described in Examples 5 and 6. Soluble expressions of these nanobodies were obtained, where Nb1 has the least protein expression concentration of 3 mg/L, while the rest of nanobodies have an average protein expression concentration of 8 mg/L.

In Western blot and ELISA, affinity was clearly shown in all 6 proteins, and the OD450 value in ELISA for 5 nanobodies, namely human lung tissues Nb11, Nb15, Nb17, Nb6 and Nb43 were 2 times greater than that of the negative control group. Immunohistochemical staining showed that these clones had strong affinity. All clones showed significant differences with the negative control group.

In vivo specificity testing in mice showed that five nanobodies, namely Nb11, NB15, NB17, NB6 and Nb43 had specificity similar to that of Nb17; while there were variations in the clustering effect, all the images exhibited obvious clustering in the lung.

Above mentioned specific embodiments of the present invention are presented for purposes of illustration and description, but is not intended to be exhaustive or limited to the invention in the form disclosed. Many modifications and variations will be apparent to those of ordinary skill in the art without departing from the scope and spirit of the invention. Thus, equality of changes and modifications without departing from the spirit and scope of the invention shall fall within the scope of the invention.

---

What is claimed is:

1. A human lung-targeting nanobody, comprising an amino acid sequence selected from the group consisting of SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, and SEQ ID NO:30.

2. A preparation comprising the nanobody of claim 1.

3. The preparation of claim 2, wherein the nanobody binds to human pulmonary surfactant protein A.

* * * * *

SEQUENCE LISTING

```
<160> NUMBER OF SEQ ID NOS: 30

<210> SEQ ID NO 1
<211> LENGTH: 486
<212> TYPE: DNA
<213> ORGANISM: Artificial Sequence
<220> FEATURE:
<223> OTHER INFORMATION: single domain antibody

<400> SEQUENCE: 1
ttgcaggccc agctggccgg tcagttgcag ctcgtggagt cggggggagg cttggtgcag        60 cctgggggt ctctgagact ctcctgtgca gcctctgaat tcactttgga ttattatgaa       120
ataggctggt tccggcaggc cccggggaag gaccgtgagg ggctctcatg tattggttat       180
agtgacagaa tcgcgtatta ttcagagtcc gtgaagggcc gattcaccac cgtcagagac       240
gacgccacga gcacggtctc tctttatatg gatatgatga ttccagagga cacaggcact       300
tattattgtg cggggtcggt tgtggagcct tacgagttac tgccagcggc tgaatatgac       360
tactggggac aggggacccg ggtcactgtc tcctcagcgc accacagcga agaccccggc       420
ccccgaggcc ttgcggccgc aggtgcgccg gtgccgtatc cggatccgct ggaaccgcgt       480
gccgca                                                                  486

<210> SEQ ID NO 2
<211> LENGTH: 450
<212> TYPE: DNA
<213> ORGANISM: Artificial Sequence
<220> FEATURE:
<223> OTHER INFORMATION: single domain antibody
```

<400> SEQUENCE: 2

```
tggcaggccc agctggccgt tcagttgcag ctcgtggagt ctgggggaga cttggcgcag      60
cctgggggt ctctgacact ctcctgtaca gcctctggaa cgttcaagat ctattccatg     120
ggctggtacc gccgccctca gcgcgagttg gtcgcgaaaa tgcttaatgg tggtgacaca     180
caatattcag actccgtgaa gggccgattc accatctcca gaaccaacaa cacgatgtat     240
ctccacatga caacctgaaa cctgaggac acggccgtct attattgtaa tctacaggat      300
tggtatagcg aacctgcggg cgactattgg ggcccgggga cccaggtcac cgtctcctca     360
gcgcaccaca gcgaagaccc cggccccga ggccttgcgg ccgcaggtgc gccggtgccg      420
tatccggatc cgctggaacc gcgtgccgca                                      450
```

<210> SEQ ID NO 3
<211> LENGTH: 330
<212> TYPE: DNA
<213> ORGANISM: Artificial Sequence
<220> FEATURE:
<223> OTHER INFORMATION: single domain antibody

<400> SEQUENCE: 3

```
atgcaggccc agctggccgg tcagttgcag ctcgtggagt ctgggggagg cttggtgcag      60
cctgggggt ctctgagact ctcctgtaca gcctctaaat tccatttgga ttcttatgcc     120
gtagcctggt tccgccagac cccagggaag gagcgtgagg cggtctcatt tataaatact     180
agtgatgatg tcacatactt tgctgactcc gtaaagggcc gattcaccat ctccagagac     240
aactccaaga acacggtata tctgcaaatg aacgtcctga accagaaga cacttctatt     300
artccggatc cgctggaacc gcgtgccgca                                      330
```

<210> SEQ ID NO 4
<211> LENGTH: 501
<212> TYPE: DNA
<213> ORGANISM: Artificial Sequence
<220> FEATURE:
<223> OTHER INFORMATION: single domain antibody

<400> SEQUENCE: 4

```
atgcaggccc agctggccgg tcagttgcag ctcgtggagt ctgggggagg cttggtgcag      60
cctgggggt ctctgagcgt ctcctgcgca gtccgaggac gcgatttgga ttattatgtc     120
atcggttggt tccgccaggc cccagggaag gagcgtgagg gtgtttcatg cattaataat     180
agtgatgata ccacatacta ttcagactcc gtgaagggcc gatttaccat ctcgagagat     240
cacgccaaga acacggtata tctccaaatg aacaacctga acctgaggga caccgccctt     300
tattactgtg cagcggattt cgatcgcctc gattttactg ttaaggctat gtgtgttatg     360
aagttctttt actactgggg ccaggggacg caggtcaccg tctcctcaga acccaagaca     420
ccaaaaccac aaggccccg aggccttgcg gccgcaggtg cgccggtgcc gtatccggat     480
ccgctggaac cgcgtgccgc a                                               501
```

<210> SEQ ID NO 5
<211> LENGTH: 486
<212> TYPE: DNA
<213> ORGANISM: Artificial Sequence
<220> FEATURE:
<223> OTHER INFORMATION: single domain antibody

<400> SEQUENCE: 5

```
atgcaggccc agctggccgt tcagttgcag ctcgtggagt caggtggagg cttggtgcag      60
```

| | |
|---|---|
| cctgggggt ctctgagact cgcctgtgca gcttctggat tcaatttgga tgattatgca | 120 |
| gacataggct ggttccgcca ggccccaggg aaggagcgtg aacgagtcct ttgtattact | 180 |
| attagtgatg gtaccacata ctatgaagac tccgggaagg gccgattctc catctccaca | 240 |
| gacatcgcca agaacacggt gtttcttcaa atggacagcc tgaaagctga ggacacagcc | 300 |
| gtttattatt gtgcaggaga tcccgcccct ttttgtctct ataacaccta tgtaccgcga | 360 |
| acctggggcc aggggaccca ggtcaccgtc tcctcggcgc accacagcga agaccccggc | 420 |
| ccccgaggcc ttgcggccgc aggtgcgccg gtgccgtatc cggatccgct ggaaccgcgt | 480 |
| gccgca | 486 |

<210> SEQ ID NO 6
<211> LENGTH: 509
<212> TYPE: DNA
<213> ORGANISM: Artificial Sequence
<220> FEATURE:
<223> OTHER INFORMATION: single domain antibody

<400> SEQUENCE: 6

| | |
|---|---|
| ctcttctaca aggtgtccag gctcaggtga agctggtgga gtctggggga ggctcggtgc | 60 |
| aggctggagg gtctctgaga ctctcctgta cagcctctgg atcagactac agatggatgt | 120 |
| acatcgcccg gtttcgccaa tgtccaggga aggagcgcga gggggtcgca gcaatttata | 180 |
| ctgatgatac tgatgatagt agtccgatct atgccacctc cgccaagggc cgattcacca | 240 |
| tctcccaaga caaggacaag aacgcggtat atctgcaaat gaacagcccg aaacctgagg | 300 |
| acactgccat gtactactgt gcggcaagag cgttcggtgg tacctggagc ttgagctccc | 360 |
| cggacgactt tagtgcctgg ggccagggga cccaggtcac cgtctcctca ggaacgaatg | 420 |
| aagtatgcaa gtggccccg aggccttgcg gccgcaggtg cgccggtgcc gtatccggat | 480 |
| ccgctggaac cgcgtgccgc atagactgt | 509 |

<210> SEQ ID NO 7
<211> LENGTH: 500
<212> TYPE: DNA
<213> ORGANISM: Artificial Sequence
<220> FEATURE:
<223> OTHER INFORMATION: single domain antibody

<400> SEQUENCE: 7

| | |
|---|---|
| tcttctacaa ggtgtccagg ctcaggtgaa gctggtggag tctgggggag gctcggtgca | 60 |
| ggctggaggg tctctgagac tctcctgtac agcctctgga tcagactaca gatggatgta | 120 |
| catcgcccgg tttcgccaat gtccagggaa ggagcgcgag ggggtcgcag caatttatac | 180 |
| tgatgatact gatgatagta gtccgatcta tgccacctcc gccaagggcc gattcaccat | 240 |
| ctcccaagac aaggacaaga acgcggtata tctgcaaatg aacagcccga aacctgagga | 300 |
| cactgccatg tactactgtg cggcaagagc gttcggtggt acctggagct tgagctcccc | 360 |
| ggacgacttt agtgcctggg gccaggggac ccaggtcacc gtctcctcag gaacgaatga | 420 |
| agtatgcaag tggccccga ggccttgcgg ccgcaggtgc gccggtgccg tatccggatc | 480 |
| cgctggaacc gcgtgccgca | 500 |

<210> SEQ ID NO 8
<211> LENGTH: 503
<212> TYPE: DNA
<213> ORGANISM: Artificial Sequence
<220> FEATURE:

<223> OTHER INFORMATION: single domain antibody

<400> SEQUENCE: 8

| | |
|---|---|
| tgctcttcta caaggtgtcc aggctcaggt gaagctggtg gagtctgggg gaggctcggt | 60 |
| gcaggctgga gggtctctga gactctcctg tacagcctct ggatcagact acagatggat | 120 |
| gtacatcgcc cggtttcgcc aatgtccagg gaaggagcgc gaggggtcg cagcaattta | 180 |
| tactgatgat actgatgata gtagtccgat ctatgccacc tccgccaagg gccgattcac | 240 |
| catctcccaa gacaaggaca agaacgcggt atatctgcaa atgaacagcc cgaaacctga | 300 |
| ggacactgcc atgtactact gtgcggcaag agcgttcggt ggtacctgga gcttgagctc | 360 |
| cccggacgac tttagtgcct ggggccaggg gacccaggtc accgtctcct caggaacgaa | 420 |
| tgaagtatgc aagtggcccc cgaggccttg cggccgcagg tgcgccggtg ccgtatccgg | 480 |
| atccgctgga accgcgtgcc gca | 503 |

<210> SEQ ID NO 9
<211> LENGTH: 508
<212> TYPE: DNA
<213> ORGANISM: Artificial Sequence
<220> FEATURE:
<223> OTHER INFORMATION: single domain antibody

<400> SEQUENCE: 9

| | |
|---|---|
| tcttctacaa ggtgtccagg ctcaggtgaa gctggtggag tctggggag gctcggtgca | 60 |
| ggctggaggg tctctgagac tctcctgtac agcctctgga tcagactaca gatggatgta | 120 |
| catcgcccgg tttcgccaat gtccaggaa ggagcgcgag gggtcgcag caatttatac | 180 |
| tgatgatact gatgatagta gtccgatcta tgccacctcc gccaagggcc gattcaccat | 240 |
| ctcccaagac aaggacaaga acgcggtata tctgcaaatg aacagcccga aacctgagga | 300 |
| cactgccatg tactactgtg cggcaagagc gttcggtggt acctggagct tgagctcccc | 360 |
| ggacgacttt agtgcctggg gccaggggac ccaggtcacc gtctcctcag gaacgaatga | 420 |
| agtatgcaag tggcccccga ggccttgcgg ccgcaggtgc gccggtgccg tatccggatc | 480 |
| cgctggaacc gcgtgccgca tagactgt | 508 |

<210> SEQ ID NO 10
<211> LENGTH: 508
<212> TYPE: DNA
<213> ORGANISM: Artificial Sequence
<220> FEATURE:
<223> OTHER INFORMATION: single domain antibody

<400> SEQUENCE: 10

| | |
|---|---|
| tcttctacaa ggtgtccagg ctcaggtgaa gctggtggag tctggggag gctcggtgca | 60 |
| ggctggaggg tctctgagac tctcctgtac agcctctgga tcagactaca gatggatgta | 120 |
| catcgcccgg tttcgccaat gtccaggaa ggagcgcgag gggtcgcag caatttatac | 180 |
| tgatgatact gatgatagta gtccgatcta tgccacctcc gccaagggcc gattcaccat | 240 |
| ctcccaagac aaggacaaga acgcggtata tctgcaaatg aacagcccga aacctgagga | 300 |
| cactgccatg tactactgtg cggcaagagc gttcggtggt acctggagct tgagctcccc | 360 |
| ggacgacttt agtgcctggg gccaggggac ccaggtcacc gtctcctcag gaacgaatga | 420 |
| agtatgcaag tggcccccga ggccttgcgg ccgcaggtgc gccggtgccg tatccggatc | 480 |
| cgctggaacc gcgtgccgca tagactgt | 508 |

<210> SEQ ID NO 11
<211> LENGTH: 486
<212> TYPE: DNA
<213> ORGANISM: Artificial Sequence
<220> FEATURE:
<223> OTHER INFORMATION: single domain antibody

<400> SEQUENCE: 11

| | | | | | |
|---|---|---|---|---|---|
| atgcaggccc | agctggccgg | tcagttgcag | ctcgtggagt | cgggggggagg | cttggtgcag | 60 |
| cctgggggt | ctctgagact | ctcctgtgca | gcctctgaat | tcactttgga | ttattatgaa | 120 |
| ataggctggt | tccggcaggc | cccggggaag | gaccgtgagg | ggctctcatg | tattggttat | 180 |
| agtgacagaa | tcgcgtatta | ttcagagtcc | gtgaagggcc | gattcaccac | cgtcagagac | 240 |
| gacgccacga | gcacggtctc | tctttatatg | gatatgatga | ttccagagga | cacaggcact | 300 |
| tattattgtg | cggggtcggt | tgtggagcct | tacgagttac | tgccagcggc | tgaatatgac | 360 |
| tactggggac | aggggacccg | ggtcactgtc | tcctcagcgc | accacagcga | agaccccggc | 420 |
| ccccgaggcc | ttgcggccgc | aggtgcgccg | gtgccgtatc | cggatccgct | ggaaccgcgt | 480 |
| gccgca | | | | | | 486 |

<210> SEQ ID NO 12
<211> LENGTH: 500
<212> TYPE: DNA
<213> ORGANISM: Artificial Sequence
<220> FEATURE:
<223> OTHER INFORMATION: single domain antibody

<400> SEQUENCE: 12

| | | | | | |
|---|---|---|---|---|---|
| tcttctacaa | ggtgtccagg | ctcaggtgaa | gctggtggag | tctgggggag | gctcggtgca | 60 |
| ggctggaggg | tctctgagac | tctcctgtac | agcctctgga | tcagactaca | gatggatgta | 120 |
| catcgcccgg | tttcgccaat | gtccaggaa | ggagcgcgag | ggggtcgcag | caatttatac | 180 |
| tgatgatact | gatgatagta | gtccgatcta | tgccacctcc | gccaagggcc | gattcaccat | 240 |
| ctcccaagac | aaggacaaga | acgcggtata | tctgcaaatg | aacagcccga | aacctgagga | 300 |
| cactgccatg | tactactgtg | cggcaagagc | gttcggtggt | acctgagct | tgagctcccc | 360 |
| ggacgacttt | agtgcctggg | gccaggggac | ccaggtcacc | gtctcctcag | gaacgaatga | 420 |
| agtatgcaag | tggcccccga | ggccttgcgg | ccgcaggtgc | gccggtgccg | tatccggatc | 480 |
| cgctggaacc | gcgtgccgca | | | | | 500 |

<210> SEQ ID NO 13
<211> LENGTH: 500
<212> TYPE: DNA
<213> ORGANISM: Artificial Sequence
<220> FEATURE:
<223> OTHER INFORMATION: single domain antibody

<400> SEQUENCE: 13

| | | | | | |
|---|---|---|---|---|---|
| tcttctacaa | ggtgtccagg | ctcaggtgaa | gctggtggag | tctgggggag | gctcggtgca | 60 |
| ggctggaggg | tctctgatac | tctcctgtac | agcctctgga | tcagactaca | gatggatgta | 120 |
| catcgcccgg | tttcgccaat | gtccaggaa | ggagcgcgag | ggggtcgcag | caatttatac | 180 |
| tgatgatact | gatgatagta | gtccgatcta | tgccacctcc | gccaagggcc | gattcaccat | 240 |
| ctcccaagac | aaggacaaga | acgcggtata | tctgcaaatg | aacagcccga | aacctgagga | 300 |
| cactgccatg | tactactgtg | cggcaagagc | gttcggtggt | acctgagct | tgagctcccc | 360 |
| ggacgacttt | agtgcctggg | gccaggggac | ccaggtcacc | gtctcctcag | gaacgaatga | 420 |

```
agtatgcaag tggccccga ggccttgcgg ccgcaggtgc gccggtgccg tatccggatc    480
cgctggaacc gcgtgccgca                                                500
```

<210> SEQ ID NO 14
<211> LENGTH: 500
<212> TYPE: DNA
<213> ORGANISM: Artificial Sequence
<220> FEATURE:
<223> OTHER INFORMATION: single domain antibody

<400> SEQUENCE: 14

```
tcttctacaa ggtgtccagg ctcaggtgaa gctggtggag tctggggag gctcggtgca      60 ggctggaggg tctctgagac tctcctgtac agcctctgga tcagactaca gatggatgta   120
catcgcccgg tttcgccaat gtccaggaa ggagcgcgag ggggtcgcag caatttatac    180
tgatgatact gatgatagta gtccgatcta tgccacctcc gccaagggcc gattcaccat   240
ctcccaagac aaggacaaga acgcggtata tctgcaaatg aacagccga aacctgagga   300 cactgccatg tactactgtg cggcaagagc gttcggtggt acctggagct tgagctcccc   360
ggacgacttt agtgcctggg gccaggggac ccaggtcacc gtctcctcag gaacgaatga   420
agtatgcaag tggccccga ggccttgcgg ccgcaggtgc gccggtgccg tatccggatc   480
cgctggaacc gcgtgccgca                                                500
```

<210> SEQ ID NO 15
<211> LENGTH: 486
<212> TYPE: DNA
<213> ORGANISM: Artificial Sequence
<220> FEATURE:
<223> OTHER INFORMATION: single domain antibody

<400> SEQUENCE: 15

```
atgcaggccc agctggccgt tcagttgcag ctcgtggagt cggggggagg cttggtgcaa    60 tctgggggt ctctgagact ctcctgtgca gcctctggat tcactttcaa tgactatcgc   120
atgagctggg tccgccaggc tccaggaaag gggctcgagt gggtctcaga tattaacagt   180
ggtggtagta gtacatacta tgcagactcc gtgaagggcc gattcaccgt ctccagagac   240
aacgccaaga acacgctgta tctgcaaatg aacagcctga aacctgagga cacggccatt   300
tactactgtg tggccctact tgggcgcggt tgttcaggct tggttcaggg ggcctttgga   360
ccctggggcc aggggaccca ggtcaccgtc tcctcggcgc accacagcga agaccccggc   420
ccccgaggcc ttgcggccgc aggtgcgccg gtgccgtatc cggatccgct ggaaccgcgt   480
gccgca                                                              486
```

<210> SEQ ID NO 16
<211> LENGTH: 162
<212> TYPE: PRT
<213> ORGANISM: Artificial Sequence
<220> FEATURE:
<223> OTHER INFORMATION: single domain antibody

<400> SEQUENCE: 16

```
Leu Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Ala Ala Ser
            20                  25                  30

Glu Phe Thr Leu Asp Tyr Tyr Glu Ile Gly Trp Phe Arg Gln Ala Pro
        35                  40                  45
```

```
Gly Lys Asp Arg Glu Gly Leu Ser Cys Ile Gly Tyr Ser Asp Arg Ile
 50                  55                  60

Ala Tyr Tyr Ser Glu Ser Val Lys Gly Arg Phe Thr Thr Val Arg Asp
 65                  70                  75                  80

Asp Ala Thr Ser Thr Val Ser Leu Tyr Met Asp Met Met Ile Pro Glu
                 85                  90                  95

Asp Thr Gly Thr Tyr Tyr Cys Ala Gly Ser Val Val Glu Pro Tyr Glu
            100                 105                 110

Leu Leu Pro Ala Ala Glu Tyr Asp Tyr Trp Gly Gln Gly Thr Arg Val
        115                 120                 125

Thr Val Ser Ser Ala His His Ser Glu Asp Pro Gly Pro Arg Gly Leu
130                 135                 140

Ala Ala Ala Gly Ala Pro Val Pro Tyr Pro Asp Pro Leu Glu Pro Arg
145                 150                 155                 160

Ala Ala
```

<210> SEQ ID NO 17
<211> LENGTH: 150
<212> TYPE: PRT
<213> ORGANISM: Artificial Sequence
<220> FEATURE:
<223> OTHER INFORMATION: single domain antibody

<400> SEQUENCE: 17

```
Trp Gln Ala Gln Leu Ala Val Gln Leu Gln Leu Val Glu Ser Gly Gly
 1                   5                  10                  15

Asp Leu Ala Gln Pro Gly Gly Ser Leu Thr Leu Ser Cys Thr Ala Ser
                20                  25                  30

Gly Thr Phe Lys Ile Tyr Ser Met Gly Trp Tyr Arg Arg Pro Gln Arg
            35                  40                  45

Glu Leu Val Ala Glu Met Leu Asn Gly Gly Asp Thr Gln Tyr Ser Asp
 50                  55                  60

Ser Val Lys Gly Arg Phe Thr Ile Ser Arg Thr Asn Asn Thr Met Tyr
 65                  70                  75                  80

Leu His Met Asn Asn Leu Lys Pro Glu Asp Thr Ala Val Tyr Tyr Cys
                 85                  90                  95

Asn Leu Gln Asp Trp Tyr Ser Glu Pro Ala Gly Asp Tyr Trp Gly Pro
            100                 105                 110

Gly Thr Gln Val Thr Val Ser Ser Ala His His Ser Glu Asp Pro Gly
        115                 120                 125

Pro Arg Gly Leu Ala Ala Ala Gly Ala Pro Val Pro Tyr Pro Asp Pro
    130                 135                 140

Leu Glu Pro Arg Ala Ala
145                 150
```

<210> SEQ ID NO 18
<211> LENGTH: 168
<212> TYPE: PRT
<213> ORGANISM: Artificial Sequence
<220> FEATURE:
<223> OTHER INFORMATION: single domain antibody

<400> SEQUENCE: 18

```
Met Gln Ala Gln Leu Ala Gly Gln Leu Gln Leu Val Glu Ser Gly Gly
 1                   5                  10                  15

Gly Leu Val Gln Pro Gly Gly Ser Leu Arg Leu Ser Cys Thr Ala Ser
                20                  25                  30
```

Lys Phe His Leu Asp Ser Tyr Ala Val Ala Trp Phe Arg Gln Thr Pro
            35                  40                  45

Gly Lys Glu Arg Glu Ala Val Ser Phe Ile Asn Thr Ser Asp Asp Val
 50                  55                  60

Thr Tyr Phe Ala Asp Ser Val Lys Gly Arg Phe Thr Ile Ser Arg Asp
 65                  70                  75                  80

Asn Ser Lys Asn Thr Val Tyr Leu Gln Met Asn Val Leu Lys Pro Glu
                85                  90                  95

Asp Thr Ser Ile Tyr Val Cys Ala Ala Val Arg Ser Pro Gly Pro Thr
            100                 105                 110

Gly Pro Ser Met Gln Pro Met Trp Val Pro Asp Leu Tyr Asp Tyr Trp
            115                 120                 125

Gly Gln Gly Thr Gln Val Thr Val Ser Ser Ala His His Ser Glu Asp
    130                 135                 140

Pro Gly Pro Arg Gly Leu Ala Ala Ala Gly Ala Pro Val Pro Tyr Pro
145                 150                 155                 160

Asp Pro Leu Glu Pro Arg Ala Ala
                165

<210> SEQ ID NO 19
<211> LENGTH: 166
<212> TYPE: PRT
<213> ORGANISM: Artificial Sequence
<220> FEATURE:
<223> OTHER INFORMATION: single domain antibody

<400> SEQUENCE: 19

Met Gln Ala Gln Leu Ala Gly Gln Leu Gln Leu Val Glu Ser Gly Gly
  1               5                  10                  15

Gly Leu Val Gln Pro Gly Gly Ser Leu Ser Val Ser Cys Ala Val Arg
             20                  25                  30

Gly Arg Asp Leu Asp Tyr Tyr Val Ile Gly Trp Phe Arg Gln Ala Pro
             35                  40                  45

Gly Lys Glu Arg Glu Gly Val Ser Cys Ile Asn Asn Ser Asp Asp Thr
 50                  55                  60

Thr Tyr Tyr Ser Asp Ser Val Lys Gly Arg Phe Thr Ile Ser Arg Asp
 65                  70                  75                  80

His Ala Lys Asn Thr Val Tyr Leu Gln Met Asn Asn Leu Lys Pro Glu
                85                  90                  95

Asp Thr Ala Leu Tyr Tyr Cys Ala Ala Asp Phe Asp Arg Leu Asp Phe
            100                 105                 110

Thr Val Lys Ala Met Cys Val Met Lys Phe Phe Tyr Tyr Trp Gly Gln
            115                 120                 125

Gly Thr Gln Val Thr Val Ser Ser Glu Pro Lys Thr Pro Lys Pro Gln
    130                 135                 140

Gly Pro Arg Gly Leu Ala Ala Ala Gly Ala Pro Val Pro Tyr Pro Asp
145                 150                 155                 160

Leu Glu Pro Arg Ala Ala
                165

<210> SEQ ID NO 20
<211> LENGTH: 162
<212> TYPE: PRT
<213> ORGANISM: Artificial Sequence
<220> FEATURE:
<223> OTHER INFORMATION: single domain antibody

<400> SEQUENCE: 20

Met Gln Ala Gln Leu Ala Val Gln Leu Val Glu Ser Gly Gly
1               5                   10                  15

Gly Leu Val Gln Pro Gly Gly Ser Leu Arg Leu Ala Cys Ala Ala Ser
            20                  25                  30

Gly Phe Asn Leu Asp Asp Tyr Ala Asp Ile Gly Trp Phe Arg Gln Ala
            35                  40                  45

Pro Gly Lys Glu Arg Glu Arg Val Leu Cys Ile Thr Ile Ser Asp Gly
50                  55                  60

Thr Thr Tyr Tyr Glu Asp Ser Gly Lys Gly Arg Phe Ser Ile Ser Thr
65                  70                  75                  80

Asp Ile Ala Lys Asn Thr Val Phe Leu Gln Met Asp Ser Leu Lys Ala
                85                  90                  95

Glu Asp Thr Ala Val Tyr Tyr Cys Ala Gly Asp Pro Ala Pro Phe Cys
            100                 105                 110

Leu Tyr Asn Thr Tyr Val Pro Arg Thr Trp Gly Gln Gly Thr Gln Val
            115                 120                 125

Thr Val Ser Ser Ala His His Ser Glu Asp Pro Gly Pro Arg Gly Leu
130                 135                 140

Ala Ala Ala Gly Ala Pro Val Pro Tyr Pro Asp Pro Leu Glu Pro Arg
145                 150                 155                 160

Ala Ala

<210> SEQ ID NO 21
<211> LENGTH: 169
<212> TYPE: PRT
<213> ORGANISM: Artificial Sequence
<220> FEATURE:
<223> OTHER INFORMATION: single domain antibody

<400> SEQUENCE: 21

Leu Leu Gln Gly Val Gln Ala Gln Val Lys Leu Val Glu Ser Gly Gly
1               5                   10                  15

Gly Ser Val Gln Ala Gly Gly Ser Leu Arg Leu Ser Cys Thr Ala Ser
            20                  25                  30

Gly Ser Asp Tyr Arg Trp Met Tyr Ile Ala Arg Phe Arg Gln Cys Pro
            35                  40                  45

Gly Lys Glu Arg Glu Gly Val Ala Ala Ile Tyr Thr Asp Asp Thr Asp
50                  55                  60

Asp Ser Ser Pro Ile Tyr Ala Thr Ser Ala Lys Gly Arg Phe Thr Ile
65                  70                  75                  80

Ser Gln Asp Lys Asp Lys Asn Ala Val Tyr Leu Gln Met Asn Ser Pro
                85                  90                  95

Lys Pro Glu Asp Thr Ala Met Tyr Tyr Cys Ala Ala Arg Ala Phe Gly
            100                 105                 110

Gly Thr Trp Ser Leu Ser Ser Pro Asp Asp Phe Ser Ala Trp Gly Gln
            115                 120                 125

Gly Thr Gln Val Thr Val Ser Ser Gly Thr Asn Glu Val Cys Lys Trp
130                 135                 140

Pro Pro Arg Pro Cys Gly Arg Arg Cys Ala Gly Ala Val Ser Gly Ser
145                 150                 155                 160

Ala Gly Thr Ala Cys Arg Ile Asp Cys
            165

<210> SEQ ID NO 22
<211> LENGTH: 169

```
<212> TYPE: PRT
<213> ORGANISM: Artificial Sequence
<220> FEATURE:
<223> OTHER INFORMATION: single domain antibody

<400> SEQUENCE: 22

Leu Leu Gln Gly Val Gln Ala Gln Val Lys Leu Val Glu Ser Gly Gly
1               5                   10                  15

Gly Ser Val Gln Ala Gly Gly Ser Leu Arg Leu Ser Cys Thr Ala Ser
            20                  25                  30

Gly Ser Asp Tyr Arg Trp Met Tyr Ile Ala Arg Phe Arg Gln Cys Pro
        35                  40                  45

Gly Lys Glu Arg Glu Gly Val Ala Ala Ile Tyr Thr Asp Asp Thr Asp
    50                  55                  60

Asp Ser Ser Pro Ile Tyr Ala Thr Ser Ala Lys Gly Arg Phe Thr Ile
65                  70                  75                  80

Ser Gln Asp Lys Asp Lys Asn Ala Val Tyr Leu Gln Met Asn Ser Pro
                85                  90                  95

Lys Pro Glu Asp Thr Ala Met Tyr Tyr Cys Ala Ala Arg Ala Phe Gly
            100                 105                 110

Gly Thr Trp Ser Leu Ser Ser Pro Asp Asp Phe Ser Ala Trp Gly Gln
        115                 120                 125

Gly Thr Gln Val Thr Val Ser Ser Gly Thr Asn Glu Val Cys Lys Trp
    130                 135                 140

Pro Pro Arg Pro Cys Gly Arg Arg Cys Ala Gly Ala Val Ser Gly Ser
145                 150                 155                 160

Ala Gly Thr Ala Cys Arg Ile Asp Cys
                165

<210> SEQ ID NO 23
<211> LENGTH: 170
<212> TYPE: PRT
<213> ORGANISM: Artificial Sequence
<220> FEATURE:
<223> OTHER INFORMATION: single domain antibody

<400> SEQUENCE: 23

Ala Leu Leu Gln Gly Val Gln Ala Gln Val Lys Leu Val Glu Ser Gly
1               5                   10                  15

Gly Gly Ser Val Gln Ala Gly Gly Ser Leu Arg Leu Ser Cys Thr Ala
            20                  25                  30

Ser Gly Ser Asp Tyr Arg Trp Met Tyr Ile Ala Arg Phe Arg Gln Cys
        35                  40                  45

Pro Gly Lys Glu Arg Glu Gly Val Ala Ala Ile Tyr Thr Asp Asp Thr
    50                  55                  60

Asp Asp Ser Ser Pro Ile Tyr Ala Thr Ser Ala Lys Gly Arg Phe Thr
65                  70                  75                  80

Ile Ser Gln Asp Lys Asp Lys Asn Ala Val Tyr Leu Gln Met Asn Ser
                85                  90                  95

Pro Lys Pro Glu Asp Thr Ala Met Tyr Tyr Cys Ala Ala Arg Ala Phe
            100                 105                 110

Gly Gly Thr Trp Ser Leu Ser Ser Pro Asp Asp Phe Ser Ala Trp Gly
        115                 120                 125

Gln Gly Thr Gln Val Thr Val Ser Ser Gly Thr Asn Glu Val Cys Lys
    130                 135                 140

Trp Pro Pro Arg Pro Cys Gly Arg Arg Cys Ala Gly Ala Val Ser Gly
145                 150                 155                 160
```

Ser Ala Gly Thr Ala Cys Arg Ile Asp Cys
              165                 170

<210> SEQ ID NO 24
<211> LENGTH: 169
<212> TYPE: PRT
<213> ORGANISM: Artificial Sequence
<220> FEATURE:
<223> OTHER INFORMATION: single domain antibody

<400> SEQUENCE: 24

Leu Leu Gln Gly Val Gln Ala Gln Val Lys Leu Val Glu Ser Gly Gly
1               5                   10                  15

Gly Ser Val Gln Ala Gly Gly Ser Leu Arg Leu Ser Cys Thr Ala Ser
            20                  25                  30

Gly Ser Asp Tyr Arg Trp Met Tyr Ile Ala Arg Phe Arg Gln Cys Pro
        35                  40                  45

Gly Lys Glu Arg Glu Gly Val Ala Ala Ile Tyr Thr Asp Asp Thr Asp
    50                  55                  60

Asp Ser Ser Pro Ile Tyr Ala Thr Ser Ala Lys Gly Arg Phe Thr Ile
65                  70                  75                  80

Ser Gln Asp Lys Asp Lys Asn Ala Val Tyr Leu Gln Met Asn Ser Pro
                85                  90                  95

Lys Pro Glu Asp Thr Ala Met Tyr Tyr Cys Ala Ala Arg Ala Phe Gly
            100                 105                 110

Gly Thr Trp Ser Leu Ser Ser Pro Asp Asp Phe Ser Ala Trp Gly Gln
        115                 120                 125

Gly Thr Gln Val Thr Val Ser Ser Gly Thr Asn Glu Val Cys Lys Trp
    130                 135                 140

Pro Pro Arg Pro Cys Gly Arg Cys Ala Gly Ala Val Ser Gly Ser
145                 150                 155                 160

Ala Gly Thr Ala Cys Arg Ile Asp Cys
              165

<210> SEQ ID NO 25
<211> LENGTH: 169
<212> TYPE: PRT
<213> ORGANISM: Artificial Sequence
<220> FEATURE:
<223> OTHER INFORMATION: single domain antibody

<400> SEQUENCE: 25

Leu Leu Gln Gly Val Gln Ala Gln Val Lys Leu Val Glu Ser Gly Gly
1               5                   10                  15

Gly Ser Val Gln Ala Gly Gly Ser Leu Arg Leu Ser Cys Thr Ala Ser
            20                  25                  30

Gly Ser Asp Tyr Arg Trp Met Tyr Ile Ala Arg Phe Arg Gln Cys Pro
        35                  40                  45

Gly Lys Glu Arg Glu Gly Val Ala Ala Ile Tyr Thr Asp Asp Thr Asp
    50                  55                  60

Asp Ser Ser Pro Ile Tyr Ala Thr Ser Ala Lys Gly Arg Phe Thr Ile
65                  70                  75                  80

Ser Gln Asp Lys Asp Lys Asn Ala Val Tyr Leu Gln Met Asn Ser Pro
                85                  90                  95

Lys Pro Glu Asp Thr Ala Met Tyr Tyr Cys Ala Ala Arg Ala Phe Gly
            100                 105                 110

Gly Thr Trp Ser Leu Ser Ser Pro Asp Asp Phe Ser Ala Trp Gly Gln

```
              115                 120                 125
Gly Thr Gln Val Thr Val Ser Ser Gly Thr Asn Glu Val Cys Lys Trp
    130                 135                 140

Pro Pro Arg Pro Cys Gly Arg Arg Cys Ala Gly Ala Val Ser Gly Ser
145                 150                 155                 160

Ala Gly Thr Ala Cys Arg Ile Asp Cys
                165

<210> SEQ ID NO 26
<211> LENGTH: 162
<212> TYPE: PRT
<213> ORGANISM: Artificial Sequence
<220> FEATURE:
<223> OTHER INFORMATION: single domain antibody

<400> SEQUENCE: 26

Met Gln Ala Gln Leu Ala Gly Gln Leu Gln Leu Val Glu Ser Gly Gly
1               5                   10                  15

Gly Leu Val Gln Pro Gly Gly Ser Leu Arg Leu Ser Cys Ala Ala Ser
            20                  25                  30

Glu Phe Thr Leu Asp Tyr Tyr Glu Ile Gly Trp Phe Arg Gln Ala Pro
        35                  40                  45

Gly Lys Asp Arg Glu Gly Leu Ser Cys Ile Gly Tyr Ser Asp Arg Ile
    50                  55                  60

Ala Tyr Tyr Ser Glu Ser Val Lys Gly Arg Phe Thr Thr Val Arg Asp
65                  70                  75                  80

Asp Ala Thr Ser Thr Val Ser Leu Tyr Met Asp Met Met Ile Pro Glu
                85                  90                  95

Asp Thr Gly Thr Tyr Tyr Cys Ala Gly Ser Val Val Glu Pro Tyr Glu
            100                 105                 110

Leu Leu Pro Ala Ala Glu Tyr Asp Tyr Trp Gly Gln Gly Thr Arg Val
        115                 120                 125

Thr Val Ser Ser Ala His His Ser Glu Asp Pro Gly Pro Arg Gly Leu
    130                 135                 140

Ala Ala Ala Gly Ala Pro Val Pro Tyr Pro Asp Pro Leu Glu Pro Arg
145                 150                 155                 160

Ala Ala

<210> SEQ ID NO 27
<211> LENGTH: 169
<212> TYPE: PRT
<213> ORGANISM: Artificial Sequence
<220> FEATURE:
<223> OTHER INFORMATION: single domain antibody

<400> SEQUENCE: 27

Leu Leu Gln Gly Val Gln Ala Gln Val Lys Leu Val Glu Ser Gly Gly
1               5                   10                  15

Gly Ser Val Gln Ala Gly Gly Ser Leu Arg Leu Ser Cys Thr Ala Ser
            20                  25                  30

Gly Ser Asp Tyr Arg Trp Met Tyr Ile Ala Arg Phe Arg Gln Cys Pro
        35                  40                  45

Gly Lys Glu Arg Glu Gly Val Ala Ala Ile Tyr Thr Asp Asp Thr Asp
    50                  55                  60

Asp Ser Ser Pro Ile Tyr Ala Thr Ser Ala Lys Gly Arg Phe Thr Ile
65                  70                  75                  80

Ser Gln Asp Lys Asp Lys Asn Ala Val Tyr Leu Gln Met Asn Ser Pro
```

```
              85                  90                  95

Lys Pro Glu Asp Thr Ala Met Tyr Tyr Cys Ala Ala Arg Ala Phe Gly
            100                 105                 110

Gly Thr Trp Ser Leu Ser Ser Pro Asp Asp Phe Ser Ala Trp Gly Gln
            115                 120                 125

Gly Thr Gln Val Thr Val Ser Ser Gly Thr Asn Glu Val Cys Lys Trp
        130                 135                 140

Pro Pro Arg Pro Cys Gly Arg Arg Cys Ala Gly Ala Val Ser Gly Ser
145                 150                 155                 160

Ala Gly Thr Ala Cys Arg Ile Asp Cys
                165

<210> SEQ ID NO 28
<211> LENGTH: 169
<212> TYPE: PRT
<213> ORGANISM: Artificial Sequence
<220> FEATURE:
<223> OTHER INFORMATION: single domain antibody

<400> SEQUENCE: 28

Leu Leu Gln Gly Val Gln Ala Gln Val Lys Leu Val Glu Ser Gly Gly
1               5                   10                  15

Gly Ser Val Gln Ala Gly Gly Ser Leu Ile Leu Ser Cys Thr Ala Ser
            20                  25                  30

Gly Ser Asp Tyr Arg Trp Met Tyr Ile Ala Arg Phe Arg Gln Cys Pro
        35                  40                  45

Gly Lys Glu Arg Glu Gly Val Ala Ala Ile Tyr Thr Asp Asp Thr Asp
    50                  55                  60

Asp Ser Ser Pro Ile Tyr Ala Thr Ser Ala Lys Gly Arg Phe Thr Ile
65                  70                  75                  80

Ser Gln Asp Lys Asp Lys Asn Ala Val Tyr Leu Gln Met Asn Ser Pro
                85                  90                  95

Lys Pro Glu Asp Thr Ala Met Tyr Tyr Cys Ala Ala Arg Ala Phe Gly
            100                 105                 110

Gly Thr Trp Ser Leu Ser Ser Pro Asp Asp Phe Ser Ala Trp Gly Gln
            115                 120                 125

Gly Thr Gln Val Thr Val Ser Ser Gly Thr Asn Glu Val Cys Lys Trp
        130                 135                 140

Pro Pro Arg Pro Cys Gly Arg Arg Cys Ala Gly Ala Val Ser Gly Ser
145                 150                 155                 160

Ala Gly Thr Ala Cys Arg Ile Asp Cys
                165

<210> SEQ ID NO 29
<211> LENGTH: 169
<212> TYPE: PRT
<213> ORGANISM: Artificial Sequence
<220> FEATURE:
<223> OTHER INFORMATION: single domain antibody

<400> SEQUENCE: 29

Leu Leu Gln Gly Val Gln Ala Gln Val Lys Leu Val Glu Ser Gly Gly
1               5                   10                  15

Gly Ser Val Gln Ala Gly Gly Ser Leu Arg Leu Ser Cys Thr Ala Ser
            20                  25                  30

Gly Ser Asp Tyr Arg Trp Met Tyr Ile Ala Arg Phe Arg Gln Cys Pro
        35                  40                  45
```

-continued

```
Gly Lys Glu Arg Glu Gly Val Ala Ala Ile Tyr Thr Asp Asp Thr Asp
    50                  55                  60

Asp Ser Ser Pro Ile Tyr Ala Thr Ser Ala Lys Gly Arg Phe Thr Ile
65                  70                  75                  80

Ser Gln Asp Lys Asp Lys Asn Ala Val Tyr Leu Gln Met Asn Ser Pro
                85                  90                  95

Lys Pro Glu Asp Thr Ala Met Tyr Tyr Cys Ala Ala Arg Ala Phe Gly
            100                 105                 110

Gly Thr Trp Ser Leu Ser Ser Pro Asp Asp Phe Ser Ala Trp Gly Gln
        115                 120                 125

Gly Thr Gln Val Thr Val Ser Ser Gly Thr Asn Glu Val Cys Lys Trp
    130                 135                 140

Pro Pro Arg Pro Cys Gly Arg Arg Cys Ala Gly Ala Val Ser Gly Ser
145                 150                 155                 160

Ala Gly Thr Ala Cys Arg Ile Asp Cys
                165

<210> SEQ ID NO 30
<211> LENGTH: 162
<212> TYPE: PRT
<213> ORGANISM: Artificial Sequence
<220> FEATURE:
<223> OTHER INFORMATION: single domain antibody

<400> SEQUENCE: 30

Met Gln Ala Gln Leu Ala Val Gln Leu Gln Leu Val Glu Ser Gly Gly
1               5                   10                  15

Gly Leu Val Gln Ser Gly Gly Ser Leu Arg Leu Ser Cys Ala Ala Ser
            20                  25                  30

Gly Phe Thr Phe Asn Asp Tyr Arg Met Ser Trp Val Arg Gln Ala Pro
        35                  40                  45

Gly Lys Gly Leu Glu Trp Val Ser Asp Ile Asn Ser Gly Gly Ser Ser
    50                  55                  60

Thr Tyr Tyr Ala Asp Ser Val Lys Gly Arg Phe Thr Val Ser Arg Asp
65                  70                  75                  80

Asn Ala Lys Asn Thr Leu Tyr Leu Gln Met Asn Ser Leu Lys Pro Glu
                85                  90                  95

Asp Thr Ala Ile Tyr Tyr Cys Val Ala Leu Leu Gly Arg Gly Cys Ser
            100                 105                 110

Gly Leu Val Gln Gly Ala Phe Gly Pro Trp Gly Gln Gly Thr Gln Val
        115                 120                 125

Thr Val Ser Ser Ala His His Ser Glu Asp Pro Gly Pro Arg Gly Leu
    130                 135                 140

Ala Ala Ala Gly Ala Pro Val Pro Tyr Pro Asp Pro Leu Glu Pro Arg
145                 150                 155                 160

Ala Ala
```